(12) United States Patent
Kimura

(10) Patent No.: US 7,978,896 B2
(45) Date of Patent: Jul. 12, 2011

(54) DATA CORRECTION APPARATUS, DATA CORRECTION METHOD, MAGNETIC RESONANCE IMAGING APPARATUS AND X-RAY CT APPARATUS

(75) Inventor: Tokunori Kimura, Yaita (JP)

(73) Assignees: Kabushiki Kaisha Toshiba, Minato-Ku, Tokyo (JP); Toshiba Medical Systems Corporation, Otawara-Shi, Tochigi-Ken (JP)

( * ) Notice: Subject to any disclaimer, the term of this patent is extended or adjusted under 35 U.S.C. 154(b) by 1098 days.

(21) Appl. No.: 11/705,063

(22) Filed: Feb. 12, 2007

(65) Prior Publication Data

US 2007/0198203 A1     Aug. 23, 2007

(30) Foreign Application Priority Data

Feb. 17, 2006    (JP) .................. 2006-041106
Dec. 8, 2006    (JP) .................. 2006-332466

(51) Int. Cl.
*G06K 9/00*    (2006.01)
(52) U.S. Cl. ...................... 382/131; 382/132
(58) Field of Classification Search .................. 382/128, 382/131, 132, 278
See application file for complete search history.

(56) References Cited

U.S. PATENT DOCUMENTS

2001/0014140 A1    8/2001   Proska et al.

FOREIGN PATENT DOCUMENTS

| JP | 9-511 | 1/1997 |
|---|---|---|
| WO | 2005/024724 A2 | 3/2005 |
| WO | 2005/024724 A3 | 3/2005 |

OTHER PUBLICATIONS

Extended European Search report dated Jun. 2, 2009 in EP 07 00 3121.
Pruessmann K. P. et al.,"Sense: Sensitivity Encoding for Fast MRI," Magnetic Resonance in Medicine, Academic Press, Duluth, MN, US, vol. 42, No. 5, Nov. 1, 1999, pp. 952-962, XP000866655.
Hayes, C. E. et al., "Volume Imaging with MR Phased Arrays," Magnetic Resonance in Medicine, Academic Press, Duluth, MN, US, vol. 18, No. 2, Apr. 1, 1991, pp. 309-319, XP000209845.

*Primary Examiner* — Vu Le
*Assistant Examiner* — Claire Wang
(74) *Attorney, Agent, or Firm* — Nixon & Vanderhye PC

(57) ABSTRACT

A data correction apparatus includes a sensitivity correction unit and an SNR distribution correcting unit. The sensitivity correction unit produces first processed data by performing sensitivity correction to first objective data obtained based on correction objective data using ununiform sensitivity distribution of a sensor for acquiring the correction objective data. The SNR distribution correcting unit produces pieces of component data each subjected to corresponding weighting depending on an SNR distribution and corresponding filtering having a mutually different intensity using second objective data obtained based on the correction objective data to produce second processed data by compounding the pieces of the component data.

23 Claims, 21 Drawing Sheets noise_scor uniform_LSI_filter nonuniform_LSI_filter uniform_structure adaptive_filter

DATA CORRECTION APPARATUS, DATA CORRECTION METHOD, MAGNETIC RESONANCE IMAGING APPARATUS AND X-RAY CT APPARATUS

BACKGROUND OF THE INVENTION

1. Field of the Invention

The present invention relates to a data correction apparatus, a data correction method, a magnetic resonance imaging apparatus and an X-ray CT (computed tomography) apparatus which correct data showing a spatially nonuniform SNR (signal to noise ratio) distribution due to a sensor's sensitivity showing a spatial distribution so that the corrected data are uniform.

2. Description of the Related Art

A MRI (Magnetic Resonance Imaging) apparatus is conventionally used as a monitoring apparatus in a medical field (see, for example, Japanese Patent No. 3,135,592).

The MRI apparatus is an apparatus which generates gradient magnetic fields by gradient coils on an imaging area of an object set in a cylindrical static field magnet for producing a static magnetic field, resonates nuclear spins in the object magnetically by transmitting RF (Radio Frequency) signals from an RF coil and reconstructs an image of the object by using NMR (Nuclear Magnetic Resonance) signals generated due to an excitation.

In the MRI apparatus of recent years, for speeding up of the imaging, an RF coil is structured of a whole body (WB) coil for transmission and a phased-array coil for reception. The phased-array coil includes a plurality of surface coils, so that it is possible to reduce the imaging time as the respective surface coils receive the NMR signals at the same time to obtain more data in a short period of time.

However, when the RF coil is structured of the phased-array coil and the WB coil, signal intensities of the image data obtained through a reconstruction processing together with the NMR signals have also nonuniformity depending on the nonuniformity of the sensitivity of the phased-array coil or the WB coil. In general, the nonuniformity of the sensitivity of the WB coil is sufficiently small at an ignorable level. However, in particular, the nonuniformity of the sensitivity of each surface coil in the phased-array coil used for each purpose is large and affects the image data.

For this reason, it is necessary to correct the nonuniformity of signal intensities of the image data due to the nonuniformity of the sensitivity of the phased-array coil.

In view of the above, up to now, prior to the main scan for generating the image of an object, the sensitivity pre-scan is executed. Then, through the sensitivity pre-scan, the image data is acquired from each of the phased-array coil and the WB coil. On the basis of the signal intensity ratio that is a division value of the signal intensities of pieces of image data, the sensitivity distribution of the phased-array coil is estimated as the three-dimensional sensitivity map data. Furthermore, the signal intensity unevenness of the image data is corrected with use of the thus acquired three-dimensional sensitivity map data of the phased-array coil.

However, in the MR imaging while using the above-mentioned plural surface coils and the MR imaging while using the single surface coil, when the sensitivity distribution of the surface coil is corrected, there is a problem in that a spatial nonuniformity occurs in the SNR. That is, before the correction, the sensitivity distribution of the surface coil is spatially nonuniform but the image noise level is constant.

Therefore, if the sensitivity distribution of the surface coil is corrected and the signal intensity of the image data depending on the space is set constant, the image noise becomes spatially nonuniform. For example, the image noise at a part where the signal intensity is amplified through the correction of the sensitivity distribution has larger intensity than the image noise at a part where the signal intensity is not emphasized. As a result, the SNR becomes spatially nonuniform, which leads to the degradation in the image quality, and thus the spatial nonuniformity of the SNR is not preferable in the diagnosis.

In addition, in a medical device such as other image diagnostic apparatus or a biological information measuring instrument other than the MRI apparatus using the surface coils as the sensors as well, if the intensities of the signals obtained while the spatially nonuniform sensitivity distribution of the sensor is collected are set constant, the spatial nonuniformity occurs in the SNR together with the noise, which may lead to the degradation in the quality of image or the measurement result.

SUMMARY OF THE INVENTION

The present invention has been made in light of the conventional situations, and it is an object of the present invention to provide a data correction apparatus, a data correction method, a magnetic resonance imaging apparatus and an X-ray CT apparatus which make it possible to obtain uniform data by correcting a spatially nonuniform sensitivity distribution of a sensor with simply processing with keeping spatial uniformity of an SNR distribution.

The present invention provides a data correction apparatus comprising: a sensitivity correction unit configured to produce first processed data by performing sensitivity correction to first objective data obtained based on correction objective data using non-uniform sensitivity distribution of a sensor for acquiring the correction objective data; and an SNR distribution correcting unit configured to produce pieces of component data each subjected to corresponding weighting depending on an SNR distribution and corresponding filtering having a mutually different intensity using second objective data obtained based on the correction objective data to produce second processed data by compounding the pieces of the component data, in an aspect to achieve the object.

The present invention also provides a data correction method comprising steps of: producing first processed data by performing sensitivity correction to first objective data obtained based on correction objective data using non-uniform sensitivity distribution of a sensor for acquiring the correction objective data; and producing pieces of component data each subjected to corresponding weighting depending on an SNR distribution and corresponding filtering having a mutually different intensity using second objective data obtained based on the correction objective data to produce second processed data by compounding the pieces of the component data, in an aspect to achieve the object.

The present invention also provides a magnetic resonance imaging apparatus comprising: a coil; a data acquisition unit configured to acquire at least one of magnetic resonance image data and k-space data of an object with said coil serving as a sensor; a sensitivity correction unit configured to produce first processed data by performing sensitivity correction to first objective data obtained based on at least one of the magnetic resonance image data and the k-space data using non-uniform sensitivity distribution of said coil; and an SNR distribution correcting unit configured to produce pieces of component data each subjected to corresponding weighting depending on an SNR distribution and corresponding filtering having a mutually different intensity using second objective data obtained based on at least one of the magnetic resonance image data and the k-space data to produce second processed data by compounding the pieces of the component data, in an aspect to achieve the object.

The present invention also provides an X-ray CT apparatus comprising: an X-ray detector; a data acquisition unit configured to acquire at least one of image data and projection data of an object with said X-ray detector serving as a sensor; a sensitivity correction unit configured to produce first processed data by performing sensitivity correction to first objective data obtained based on at least one of the image data and the projection data using non-uniform sensitivity distribution of said X-ray detector; and an SNR distribution correcting unit configured to produce pieces of component data each subjected to corresponding weighting depending on an SNR distribution and corresponding filtering having a mutually different intensity using second objective data obtained based on at least one of the image data and the projection data to produce second processed data by compounding the pieces of the component data, in an aspect to achieve the object.

The data correction apparatus, the data correction method, the magnetic resonance imaging apparatus and the X-ray CT apparatus as described above make it possible to obtain uniform data by correcting a spatially nonuniform sensitivity distribution of a sensor with simply processing with keeping spatial uniformity of an SNR distribution.

DESCRIPTION OF THE PREFERRED EMBODIMENTS

A data correction apparatus, a data correction method, a magnetic resonance imaging apparatus and an X-ray CT apparatus according to embodiments of the present invention will be described with reference to the accompanying drawings.

Figure 1:
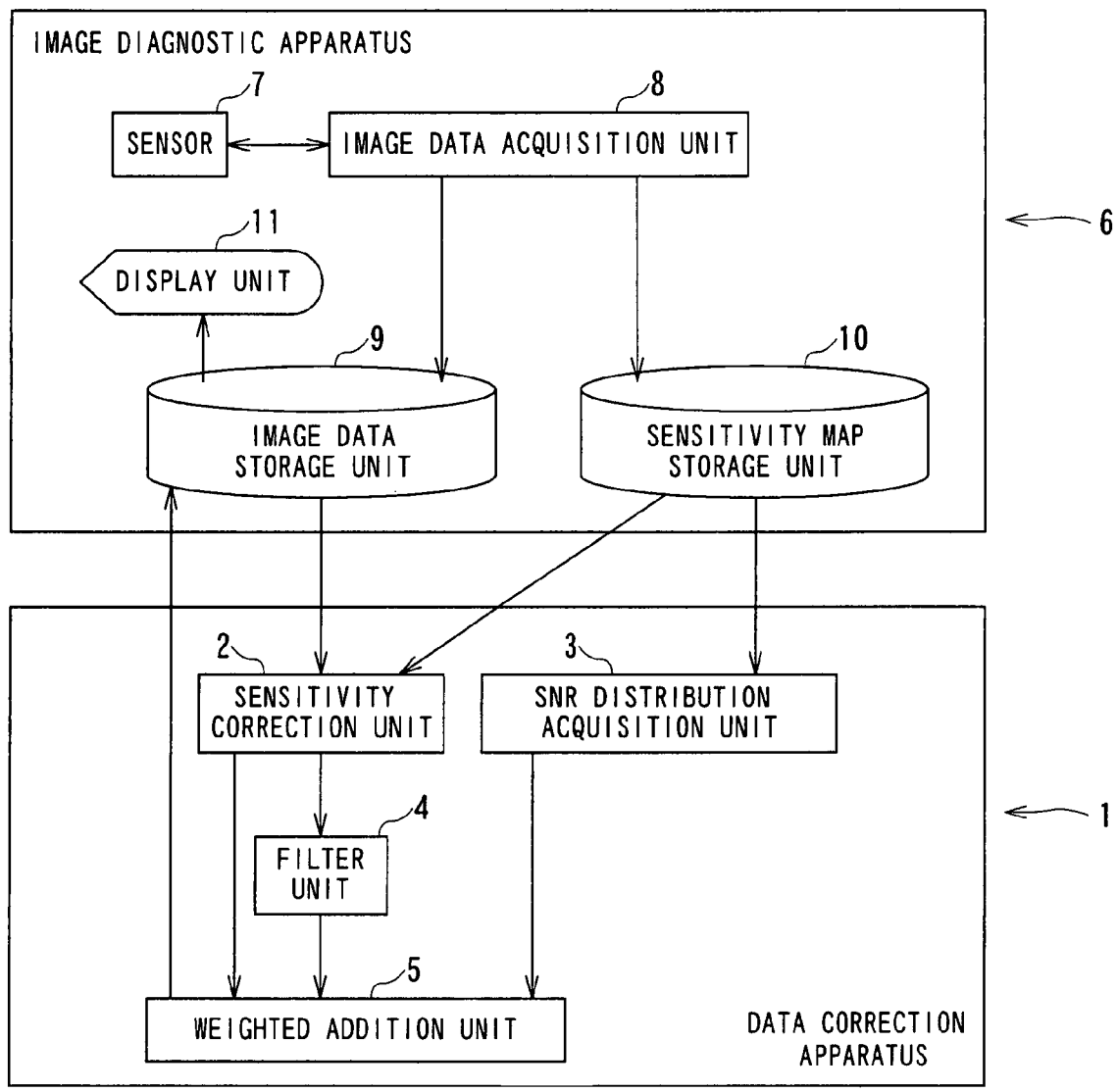
FIG. 1 is functional block diagram showing a data correction apparatus according to a first embodiment of the present invention.

FIG. 1 is a functional block diagram showing a data correction apparatus according to a first embodiment of the present invention.

A data correction apparatus 1 is structured by a computer reading a program. It should be noted that an entirety or a part of the data correction apparatus 1 may be structured by a circuit. The data correction apparatus 1 includes a sensitivity correction unit 2, an SNR distribution acquisition unit 3, a filter unit 4 and weighted addition unit 5. Thus, these elements give, to the data correction apparatus 1, a function to acquire uniform data by performing correction processing of a spatially nonuniform sensitivity distribution of a sensor with keeping spatial uniformity of an SNR distribution to data acquired by a medical apparatus like an image diagnostic apparatus and a measuring device for living body information.

Examples of a medical apparatus for collecting the data that is the correction target includes a biological information measuring instrument such as an electroencephalograph, an electrocardiograph, and a synchronoscope, and an image diagnostic apparatus such as an ultrasonic diagnostic apparatus, an X-ray diagnostic apparatus, an X-ray CT apparatus, a magnetic resonance imaging apparatus, or a nuclear medical diagnostic apparatus. A sensor of the magnetic resonance imaging apparatus is a coil. Each sensor of the X-ray diagnostic apparatus, the X-ray CT apparatus and the nuclear medical diagnostic apparatus such as a SPECT (single photon emission computed tomography), or a PET (positron emission computed tomography) is a detection element. The detection element of the X-ray diagnostic apparatus, the X-ray CT apparatus, or the nuclear medical diagnostic apparatus has types including a direct conversion type and an indirect conversion type. With either of the types, the detection element has a nonuniform sensitivity and the sensitivity correction needs to be performed. The sensor of the ultrasonic diagnostic apparatus is a probe provided with a plurality of ultrasonic transducers.

According to the data correction apparatus 1, not only the image data collected by the image diagnostic apparatus but also various data requiring the sensitivity correction due to the non-uniform sensitivity distribution of the sensor can be set as the correction targets. For example, when the medical apparatus for collecting the correction target data is the magnetic resonance imaging apparatus, not only the MR image data but also the k-space data can be set as the correction targets. In addition, when the medical apparatus for collecting the correction target data is the X-ray CT apparatus, not only the X-ray CT image data but also projection data can be set as the correction target.

Then, the data that is the correction target of the data correction apparatus 1 can be set as data of any dimension. For example, one-dimensional data, two-dimensional data, three-dimensional data, or four-dimensional data representing the spatial position and time can be set as the correction target of the data correction apparatus 1. Examples of data having the temporal dimension include data having the time axis acquired in the electroencephalograph, the electrocardiograph, the synchronoscope, or the ultrasonic diagnostic apparatus. In addition, T1 weighted image data obtained with use of a T1 relaxation (longitudinal relaxation) time difference and T2 weighted image data obtained with use of a T2 relaxation (transverse relaxation) time difference in the MRI apparatus are also the examples of the data having the temporal dimension. The T1 weighted image data and the T2 weighted image data attenuate with the elapse of time. If the sensitivity correction of the coil is performed, the noise becomes nonuniform in terms of time. For this reason, the correction processing on the data also in the time axis direction needs to be performed.

Hereinafter, a description will be given of an example in which the data that is the correction target is image data collected in an image diagnostic apparatus 6. The image diagnostic apparatus 6 includes a sensor 7, an image data acquisition unit 8, an image data storage unit 9, a sensitivity map storage unit 10, and the display unit 11. The sensor 7 is configured to detect data under a control by the image data acquisition unit 8 and supply the detected data to the image data acquisition unit 8.

The image data acquisition unit 8 is provided with a function of collecting data by controlling the sensor 7 and generating image data from the collected data. The image data storage unit 9 includes a function of storing the image data generated by the image data acquisition unit 8. The sensitivity map storage unit 10 has a function of storing a sensitivity map representing a spatial or temporal sensitivity distribution of the sensor 7. The display unit 11 includes a display and has a function of displaying the image data read from the image data storage unit 9 on the display.

The sensitivity map stored in the sensitivity map storage unit 10 may be obtained through estimation or measurement based on an arbitrary method. In particular, by performing the data collection for the sensitivity map measurement with use of the sensor 7, it is also possible to generate a sensitivity map on the basis of the collected data.

The sensitivity correction unit 2 of the data correction apparatus 1 has a function of acquiring original image data that is a target of the sensitivity correction from the image data storage unit 9 and also acquiring a sensitivity map to be used for the sensitivity correction from the sensitivity map storage unit 10 to obtain sensitivity correction image data through sensitivity correction on the original image data while using the sensitivity map and a function of supplying the thus obtained sensitivity correction image data to the filter unit 4 and the weighted addition unit 5.

The SNR distribution acquisition unit 3 has a function of acquiring or estimating the distribution of the SNR generated along with the sensitivity correction on the original image data on the basis of an arbitrary method to supply the distribution information on the SNR to the weighted addition unit 5. The distribution information on the SNR can be set as, for example, an SNR distribution window representing the distribution of the SNR. The distribution information on the SNR can be estimated from the sensitivity map stored in the sensitivity map storage unit 10. In view of the above, the SNR distribution acquisition unit 3 is provided with a function of acquiring the sensitivity map from the sensitivity map storage unit 10.

In addition, the distribution information on the SNR can also be calculated by performing various image processing such as a low-pass filter and a threshold processing with respect to the original image data or the sensitivity correction image data after the sensitivity correction that is the correction target of the nonuniformly distributing SNR. Also, as another example, by comparing the original image data that is the correction target with separately acquired image data of a phantom, it is also possible to obtain the distribution information on the SNR. Therefore, the SNR distribution acquisition unit 3 can also be provided with an image processing function for calculating such distribution information on the SNR. In addition to this function, the SNR distribution acquisition unit 3 may be provided with a function of measuring the distribution of the SNR or a function of inputting the previously measured distribution of the SNR.

The filter unit 4 a function of generating the filtered image data or the filtered data by performing filter processing with use of a uniform filter on the sensitivity correction image data received from the sensitivity correction unit 2 or the sensitivity correction data obtained through the conversion of the sensitivity correction image data and a function of supplying the thus generated filtered image data or the filtered image data obtained through conversion of the filtered data to the weighted addition unit 5. An arbitrary number of uniform filters having filtering intensities different to each other are provided to the filter unit 4 when necessary. Then, the filter unit 4 is configured to generate the single filtered image data subjected to the filter processing based on the uniform filter or plural pieces of the filtered image data subjected to the filter processing based on the uniform filters having the filtering intensities different to each other.

Herein, the sensitivity correction image data that is the filter processing target has been subjected to the sensitivity correction, and therefore the SNR is non-uniform spatially or temporally. However, the uniform filter can be composed of a general-use normal filter to be applied to data of which the SNR is assumed to be constant. That is, almost all the filters of which characteristics can be considered to be uniform spatially and/or temporally in a large sense can be applied as the uniform filters. For example, linear filters each having a uniform kernel (filter intensity) to have intensities unchanged temporally and spatially or structure adaptive type filters of which the kernel is determined according to the data structure can compose the uniform filters.

Also, the data that is the filter processing target may be real space data on an r-space (real space) or k-space data on a k-space obtained in the MRI apparatus. When the k-space data is set as the filter processing target, the sensitivity correction image data is converted through FT (Fourier transform) into the sensitivity correction k-space data, and the sensitivity correction k-space data becomes the filter processing target. Then, the filter processing k-data after the filter processing is converted through FT into the filtered image data to be supplied to the weighted addition unit 5.

Furthermore, a particular FREBAS (Fresnel transform Band Split) space in which a frequency band is split with the application of Fresnel transform and the Wiener Filter of an SNR adaptive type in which the filter intensity is determined so that the SNR becomes optimal in the processing space are proposed. The Wiener Filter can set a space obtained by dividing the Fourier space or the real space through Wavelet transform other than the FREBAS space as the processing space. In particular, if the FREBAS space is set as the processing space of the Wiener Filter, the kernel of the uniform filter to the data on the FREBAS space can be determined appropriately as by monitoring noise.

In view of the above, the sensitivity correction image data is converted into the sensitivity correction FREBAS space data and the filter processing FREBAS space data subjected to the filter processing based on the wiener Filter is converted into the filtered image data, which may be supplied to the weighted addition unit 5. The FREBAS space is a space used for an analysis based on Multi-Resolution Analysis method with use of the multiple solution of the Fresnel transform or the band split as one of the improvement methods for the SNR.

Note that, detail of the structure adaptive filter is described on Chen, H. G., A. Li, L. Kaufman, and J. Hale, "A fast filtering algorithm for image enhancement", IEEE Trans. Medical Imaging 13(3):557-564 (1994). Detail of Wiener Filter is described on Ito S, Yamada Y, "Use of Dual Fresnel Transform Pairs to Improve Signal-to-Noise Ratio in Magnetic Resonance Imaging", Med Imag Tech 19(5), 355-369 (2001).

The weighted addition unit 5 has a function of performing weighted addition on the single or the plural pieces of the filtered image data received from the filter unit 4 and the sensitivity correction image data before the filter processing received from the sensitivity correction unit 2 on the basis of the SNR distribution information such as the SNR distribution window received from the SNR distribution acquisition unit 3 to generate nonuniformity filtered image data substantially equivalent to the image data subjected to the film processing based on the nonuniform filter and a function of writing the thus generated nonuniformity filtered image data in the image data storage unit 9 of the image diagnostic apparatus 6. It should be noted that the sensitivity correction image data before the filter processing is not set as the target of the weighted addition and only the plural pieces of the filtered image data received from the filter unit 4 may be set as the targets of the weighted addition. In other words, the plural pieces of the filtered image data subjected to the filtering with the different intensities may be set as the targets of the weighted addition.

Next, a description will be given of an operation and an action of the data correction apparatus 1.

Figure 2:
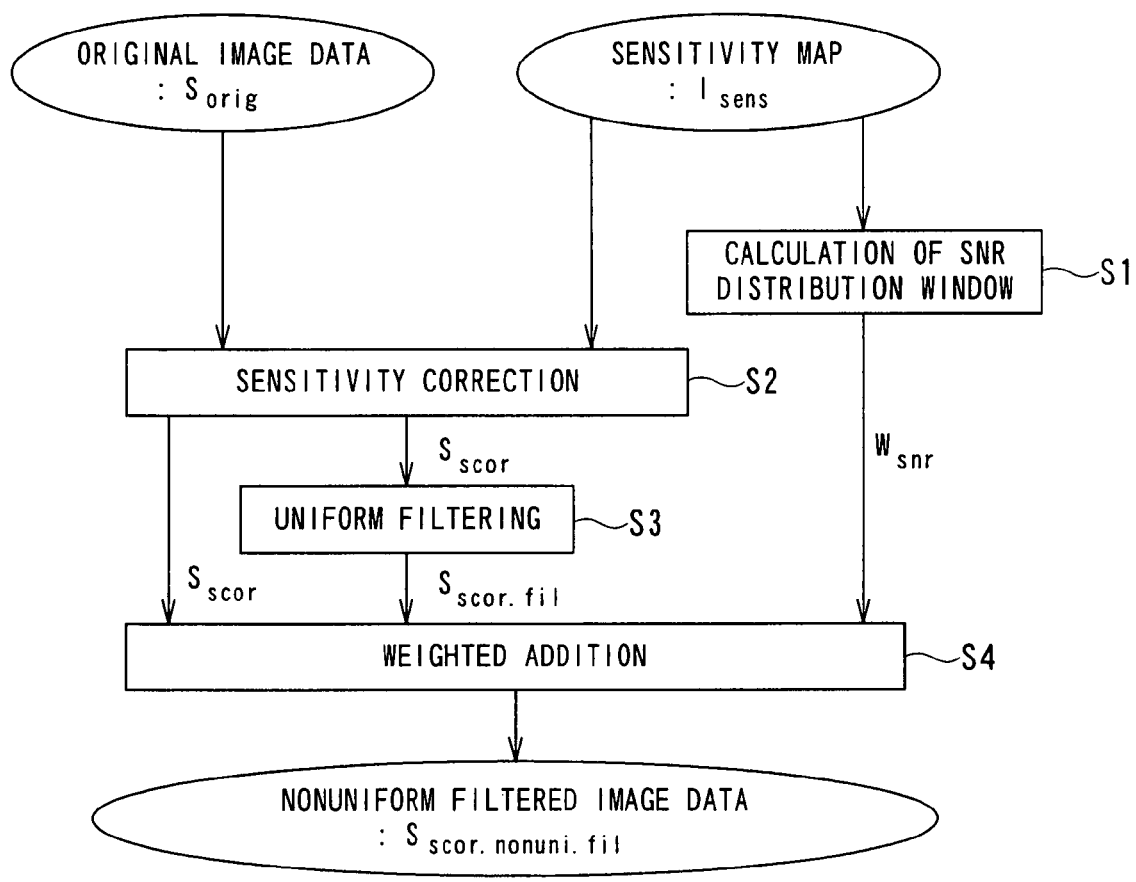
FIG. 2 is a flowchart showing a procedure of performing sensitivity correction to image data acquired from the image diagnostic apparatus with keeping an SNR distribution uniform by the data correction apparatus shown in FIG. 1.

FIG. 2 is a flowchart showing a procedure of performing sensitivity correction to image data acquired from the image diagnostic apparatus 6 with keeping an SNR distribution uniform by the data correction apparatus 1 shown in FIG. 1. The symbols including S with a number in FIG. 2 indicate each step of the flowchart.

First of all, image data is collected in the image diagnostic apparatus 6 in advance. That is, on the basis of the control from the image data acquisition unit 8, the data for the image generation is detected by the sensor 7. The detected data is supplied from the sensor 7 to the image data acquisition unit 8, and the image data acquisition unit 8 generates the image data from this data. Then, the generated image data is written in the image data storage unit 9 and stored as original image data $S_{orig}$. At the same time, the temporal and/or spatial sensitivity distribution of the sensor 7 is estimated or measured according to an arbitrary method. The thus obtained sensitivity distribution of the sensor 7 is written in the sensitivity map storage unit 10 and stored as a sensitivity map $I_{sens}$.

Then, in Step S1, the SNR distribution acquisition unit 3 acquires from the sensitivity map storage unit 10 the sensitivity map $I_{sens}$ used for the sensitivity correction, and obtains the distribution information on the SNR on the basis of the sensitivity map $I_{sens}$. The distribution information on the SNR is set as a weighting function $W_{snr}$ functioning as the SNR distribution window and the weighting function $W_{snr}$ is supplied to the weighted addition unit 5.

If the sensitivity map $I_{sens}$ is spatially distributed in the three-dimensional manner of the x direction, the y direction, and the z direction, the sensitivity map $I_{sens}$ can be generalized and represented as $I_{sens}$ (x, y, z). In the case where the image diagnostic apparatus 6 is the MRI apparatus, the sensitivity map $I_{sens}$ (x, y, z) becomes real space (r-space) data representing the coil sensitivity distribution.

The weighting function $W_{snr}$ (x, y, z) representing the distribution of the SNR can be obtained through various methods from the normalized sensitivity map $I_{sens}$ (x, y, z) of the sensor 7. For example, in the case where only a maximum value max $[I_{sens}$ (x, y, z)] of the sensitivity map $W_{snr}$ (x, y, z) of the sensor 7 is standardized and the maximum value of the weighting function $W_{snr}$ (x, y, z) is set to 1, the weighting function $W_{snr}$ (x, y, z) can be determined based on Expression (1).

$$W_{snr}(x,y,z) = I_{sens}(x,y,z)/\max[I_{sens}(x,y,z)] \quad (1)$$

wherein $W_{snr}(x,y,z)$: a weighting function (an SNR distribution function).

In addition, for instance, in the case where the maximum value of the weighting function $W_{snr}$ (x, y, z) is set to 1 and also the minimum value of the weighting function $W_{snr}$ (x, y, z) is set to 0, a minimum value min $[I_{sens}$ (x, y, z)] of the sensitivity map $I_{sens}$ (x, y, z) of the sensor 7 is also used, thereby making it possible to determine the weighting function $W_{snr}$ (x, y, z) based on Expression (2).

$$W_{snr}(x, y, z) = \{I_{sens}(x, y, z) - \min[I_{sens}(x, y, z)]\} / \{\max[I_{sens}(x, y, z)] - \min[I_{sens}(x, y, z)]\} \quad (2)$$

Also, in the MRI apparatus, when the parallel imaging (PI) is performed by using a plurality of multi coils and the original image data $S_{orig}$ is synthesized while signals from the multi coils are unfolded, it is possible to obtain the weighting function $W_{snr}$ (x, y, z) as shown in Expression (3) from a g-factor distribution g (x, y, z) defined for determining the noise distribution in consideration of sensitivity of the multi coil having the coil independency or the influence of the synthesis with the signal unfolding.

$$W_{snr}(x,y,z) = 1/g(x,y,z) \quad (3)$$

Next, in Step S2, the sensitivity correction unit 2 acquires the original image data $S_{orig}$ that is the target of the sensitivity correction from the image data storage unit 9 and on the other hand acquires the sensitivity map $I_{sens}$ used for the sensitivity correction from the sensitivity map storage unit 10, and uses the acquired sensitivity map $I_{sens}$ to perform the sensitivity correction of the sensor 7 to the original image data $S_{orig}$, thereby obtaining a sensitivity correction image data $S_{scor}$. Then, the sensitivity correction unit 2 supplies the thus obtained sensitivity correction image data $S_{scor}$ to the filter unit 4 and the weighted addition unit 5.

The sensitivity correction image data $S_{scor}$ can be generated on the basis of Expression (4).

$$S_{scor}(x,y,z) = S_{orig}(x,y,z)/I_{sens}(x,y,z) \quad (4)$$

wherein $I_{sens}(x,y,z)$: sensitivity map data $S_{orig}(x,y,z)$: original image data (image data before sensitivity correction) and $S_{scor}(x,y,z)$: sensitivity corrected image data.

Next, in Step S3, the filter unit 4 performs the filter processing with use of the uniform filter to the sensitivity correction data on the k-space or the FREBAS space obtained through the conversion of the sensitivity correction image data $S_{scor}$ or the sensitivity correction image data $S_{scor}$ received from the sensitivity correction unit 2, thereby generating the filtered image data $S_{scor.fil}$ or the filtered data.

When the filtered data other than the filtered image data $S_{scor.fil}$ is generated, the filtered data is converted into the filtered image data $S_{scor.fil}$.

Then, the filter unit 4 supplies the thus obtained filtered image data $S_{scor.fil}$ to the weighted addition unit 5. As a result, the weighted addition unit 5 has at least the sensitivity correction image data $S_{scor}$ before the filter processing and the filtered image data $S_{scor.fil}$ after the filter processing. In the case where the plural pieces of the filtered image data $S_{scor.fil}$ are generated on the basis of the filtering of different intensities in the filter unit 4, the same number of pieces of the filtered image data $S_{scor.fil}$ as that of types of the filtering intensities are supplied to the weighted addition unit 5.

Here, a description will be given of the most simple calculation example while it is assumed that the sensitivity correction image data $S_{scor}$ is formed of two components and only component having bad SNR is subjected to smoothing by filtering in the filter unit 4. In practice, it may suffice that only the component having bad SNR is subjected to smoothing.

When H denotes a Filter operator, the filtered image data $S_{scor.fil}$ can obtain image data in which the smoothing filter is applied to the entirety of the sensitivity correction image data $S_{scor}$ on the basis of Expression (5).

$$S_{scor.fil}(x,y,z) = H[S_{scor}(x,y,z)] \quad (5)$$

Next, in Step S4, the weighted addition unit 5 receives the weighting function $W_{snr}$ in accordance with the distribution of the SNR from the SNR distribution acquisition unit 3, and uses the weighting function $W_{snr}$ to synthesize the single or the plural pieces of the filtered image data $S_{scor.fil}$ received from the filter unit 4, and the sensitivity correction image data $S_{scor}$ before the filter processing received from the sensitivity correction unit 2 through weighted addition, thereby generating a nonuniformity filtered image data $S_{scor.nonuni.fil}$.

The weighting with use of the weighting function $W_{snr}$ is executed as shown in Expression (6-1) and Expression (6-2). That is, the weighting is applied such that the filtering is performed on only the component having bad SNR. As a result of this weighting, the sensitivity correction image data $S_{scor}$ is substantially divided into a component having good SNR $S_{scor.h}$ (x, y, z) and a filtered component having bad SNR $S_{scor.l.fil}$ (x, y, z).

$$S_{scor.h}(x,y,z) = W_{snr}(x,y,z) * S_{scor}(x,y,z) \quad (6-1)$$

$$S_{scor.l.fil}(x,y,z) = \{1 - W_{snr}(x,y,z)\} * S_{scor.fil}(x,y,z) \quad (6-2)$$

Subsequently, the two components of the component having good SNR $S_{scor.h}$ (x, y, z) and the filtered component having bad SNR $S_{scor.l.fil}$ (x, y, z) are synthesized to each other as shown in Expression (7), thereby obtaining image data (nonuniformity filtered image data) $S_{scor.nonuni.fil}$ (x, y, z) subjected to the nonuniform SNR correction filter processing as the final correction image.

$$S_{scor.nonuni.fil}(x,y,z) = S_{scor.h}(x,y,z) + S_{scor.l.fil}(x,y,z) \quad (7)$$

The thus generated nonuniformity filtered image data $S_{scor.nonuni.fil}$ is written in the image data storage unit 9 of the image diagnostic apparatus 6. After that, the display unit 11 displays the nonuniformity filtered image data $S_{scor.nonuni.fil}$ read from the image data storage unit 9 on the display. As a result, the user can confirm the nonuniformity filtered image data $S_{scor.nonuni.fil}$ that has been subjected to the sensitivity correction so that the SNR distribution becomes uniform.

It should be noted that only the filtered image data $S_{scor.fil}$ filtered by the uniform filters having different intensities may be set as the targets of the weighted addition. In other words, the filtering intensity of the component having good SNR $S_{scor,h}$ (x, y, z) that is the target of the weighted addition may be set to an intensity other than 0. In this case, the sensitivity correction image data $S_{scor}$ is not supplied from the sensitivity correction unit 2 to the weighted addition unit 5.

In other words, the data correction apparatus 1 having the above-mentioned structure is adapted to use the estimated or measured information on the spatial distribution or time distribution of the sensitivity of the sensor 7 such as a coil, generate a plurality of pieces of data by performing the uniform filtering having different intensities, which is the smoothing mainly, on the data after the sensitivity correction such as the image data in accordance with the degree of the sensitivity nonuniformity, and perform the weighted addition of the pieces of the thus generated data mutually so that the SNR and the smoothing intensities are in the inverse correlation on the basis of the SNR distribution information. That is, for the filtering, instead of using a normal filter used for the data in which the SNR distribution is constant, such an addition is performed to the data having the small SNR that the weight of the data with the strong smoothing becomes large and on the contrary the weight of the data with the weak smoothing becomes small. It should be noted that the data in which the filter processing is not performed can be considered as the data in which the filter processing with zero intensity is performed.

For this reason, according to the data correction apparatus 1, the correction of the spatially nonuniform sensitivity distribution of the sensor 7 is performed through a simple processing while the spatial uniformity of the SNR distribution is maintained, thereby making it possible to obtain uniform image data.

Up to now, as described above, when the sensitivity correction is performed on the data, there is a problem in that the SNR distribution becomes nonuniform. To cope with this problem, a method of performing the smoothing on the data with use of filters having varied spatial weights is considerable. In this case, in order to determine the weights of the filters, it is necessary to obtain the noise distribution through the extraction of the low frequency component from the original image or obtain the noise distribution in advance through a separate pre-scan. For example, in the MRI apparatus, the sensitivity distribution of the coil measured by the pre-scan and the noise distribution called g-factor which is determined depending on the independence of the multi coil can be used. Then, a method of smoothly changing the weights of the filters in accordance with the noise distribution function in the real space is considerable.

However, according to the method of changing the weights of the filters in the real space, that is, the kernel in accordance with the noise distribution function as needed, there is a problem in that the processing and the filter structure are complicated. In particular, when the support size of the filter is large, the increase in the processing time occurs, and the processing for the edge of the image becomes complicated. Also, according to this method, the nonuniform SNR can be corrected but it is difficult to obtain parameters such as the optimal filter weight distribution or the smoothing intensity, and it is also difficult to cause the filter weight distribution to optimally follow the SNR distribution varying for every data.

In contrast, the data correction apparatus 1 shown in FIG. 1 adopts a correction method in which the data is corrected in a simple processing such as filtering with use of a normal uniform filter while the data having the uniform SNR distribution is set as the target or weighted addition without changing the kernel of the filter in accordance with the SNR distribution on a case-by-case basis. The uniform filter is a filter of a high general versatility using the same kernel in which it is not necessary to refer to the spatial or temporal the SNR distribution.

Also, even when the uniform filter having the same smoothing intensity is used for certain data that is the filtering target, the plural pieces of data which are respectively filtered at different smoothing intensities are added at weights in accordance with the SNR distribution after the filter processing. Therefore, when each of the data obtained by the addition is considered, the smoothing intensity has the spatial distribution and the temporal distribution in accordance with SNR. Therefore, with use of the uniform filter, it is possible to perform the filtering which is equivalent to the filtering by the nonuniform filter that changes the kernel intensity in accordance with the spatially or temporally distributing SNR.

For this reason, it is unnecessary to use other step-by-step filters for the pre-processing and the adjustment, and therefore it is possible to provide an optimal image through the filtering by using the single type of the uniform filters. As a result, according to the data correction apparatus 1, not only the filter structure is relatively simple and the mounting of the filter is relatively easy but also the high speed processing can be performed. In other words, according to the data correction apparatus 1, the problems such as the complication of the above-mentioned filter structure and the increase in the processing time can be avoided.

In addition, if the structure adaptive filter, the SNR adaptive filter represented by the Wiener Filter, and a filter obtained by combining the structure adaptive filter with the SNR adaptive filter are adapted for the uniform filter used in the data correction apparatus 1, it is possible to optimally control the filter characteristics while the variation in the SNR distribution of the target data is absorbed.

It should be noted that if the data filtering is performed with use of a simple Linear Space Invariant (LSI) filer, the degradation occurs in the spatial resolution after the filter processing, and accordingly the spatially or temporally nonuniform data may be generated.

In view of the above, in particular, if a filter in which the degradation in the spatial resolution can be minimized, that is, a filter such as the Wiener Filter or the structure adaptive filter in which the image space is not divided into plural pieces and the real space is substantially preserved and at the same time a consideration is given to the noise distribution is used for the uniform filter, the above-mentioned problem such as the degradation in the spatial resolution after the filter processing can be solved even for the data in which there is a spatial distribution or a temporal distribution in the SNR. In addition, if the filter such as the structure adaptive filter or the Wiener Filter is used, in accordance with the spatial distribution and the temporal distribution of SNR, the SNR can be improved.

The filter processing to the data obtained in the MRI apparatus can be performed not only in the r-space but also in k-space. For this reason, in particular, when the parallel imaging that is a high speed imaging method with use of a multi coil in the MRI apparatus is performed, it is possible to achieve the shortening in the processing time. For example, in the case where a processing of a SMASH (Simultaneous acquisition of spatial harmonics) type, such as GRAPPA (Generalized autocalibrating partially parallel acquisitions), which is a type performing data processing in the k-space is performed, the filter processing can be performed in the k-space and thus the high speed processing can be conducted. Also, even when a processing according to a SENSE (Sensitivity Encoding) type is performed, the number of times for performing FFT (Fast Fourier Transform) is two, and thus the processing speed is high in total.

In this way, the uniform filter is easy for the processing in the complex space and superior in the SNR improvement performance in the low SNR section to the processing in the absolute value space, and is therefore advantageous in terms of mounting with respect to the MRI apparatus where the complex data processing is difficult in the r-space.

Furthermore, the data correction apparatus 1 can conduct the sensitivity correction on the sensor 7 to the normal data in which the SNR is constant temporally and spatially. This is because, when the sensitivity distribution is flat, the weights of the respective data subjected to the filtering become constant, and only the filtered data through the uniform filter becomes the data after the sensitivity correction. For this reason, if the sensitivity distribution of the sensor 7 can be obtained, in the processing performed in the data correction apparatus 1, it is unnecessary to consider on a state of the sensitivity distribution as to whether or not the sensitivity distribution is constant. Therefore, the usability in terms of mounting of the filter is high.

Figure 3:
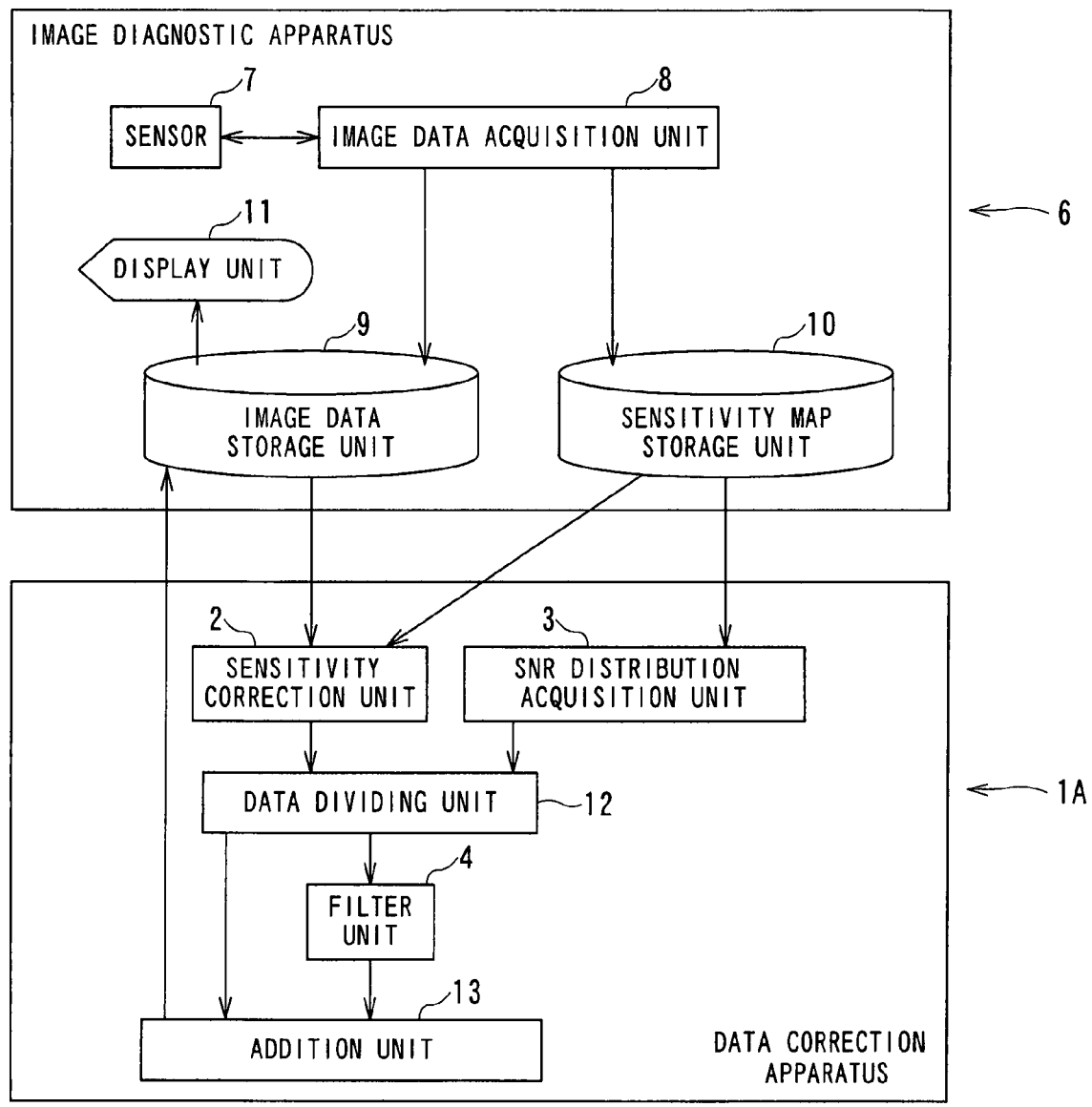
FIG. 3 is a functional block diagram showing a data correction apparatus according to a second embodiment of the present invention.

FIG. 3 is a functional block diagram showing a data correction apparatus according to a second embodiment of the present invention.

In the data correction apparatus 1A shown in FIG. 3, constructions including a data dividing unit 12 and an addition unit 13 instead of the weighted addition unit 5 are different from those of the data correction apparatus 1 shown in FIG. 1. Other constructions and operations of the data correction apparatus 1A are not different from those of the data correction apparatus 1 shown in FIG. 1 substantially. Therefore, same number is attached to a same component as that of the data correction apparatus 1 and explanation thereof is omitted.

Specifically, the data correction apparatus 1A includes a data dividing unit 12 and an addition unit 13 in addition to the sensitivity correction unit 2, the SNR distribution acquisition unit 3 and the filter unit 4. Then, the sensitivity correction unit 2 is configured to supply the sensitivity correction image data to the data dividing unit 12 and the SNR distribution acquisition unit 3 is configured to supply the distribution information on the SNR to the data dividing unit 12.

The data dividing unit 12 has a function of generating plural pieces of sensitivity correction image component data on the basis of the distribution information on the SNR related to the image data obtained from the SNR distribution acquisition unit 3 from the sensitivity correction image data acquired from the sensitivity correction unit 2 and a function of supplying a part of the thus generated sensitivity correction image component data to the filter unit 4 and supplying the remaining or another part of the sensitivity correction image component data to the addition unit 13. To be more specific, the data dividing unit 12 uses the weighted addition function to divide the sensitivity correction image data into the sensitivity correction image component data having the larger SNR and the sensitivity correction image component data having the smaller SNR on the image space. The single or plurality of sensitivity correction image component data having the large SNR is supplied to the addition unit 13 and on the other hand the single or plurality of sensitivity correction image component data having the small SNR is supplied to the filter unit 4.

The filter unit 4 is configured to use the uniform filter to perform the filtering on the sensitivity correction image component data having the small SNR or the sensitivity correction component data obtained through the conversion of the sensitivity correction image component data having the small SNR, thereby generating the filtered image data or the filtered data. Then, the thus generated filtered image data or the filtered image data obtained through the conversion of the filtered data is supplied to the addition unit 13.

The addition unit 13 has a function of generating the nonuniformity filtered image data substantially equivalent to the image data subjected to the filter processing with use of the nonuniform filter through the addition of the sensitivity correction image component data received from the data dividing unit 12 and the filtered image data received from the filter unit 4 for synthesis and a function of writing the thus generated nonuniformity filtered image data in the image data storage unit 9 of the image diagnostic apparatus 6.

Next, a description will be given of an operation and an action of the data correction apparatus 1A.

Figure 4:
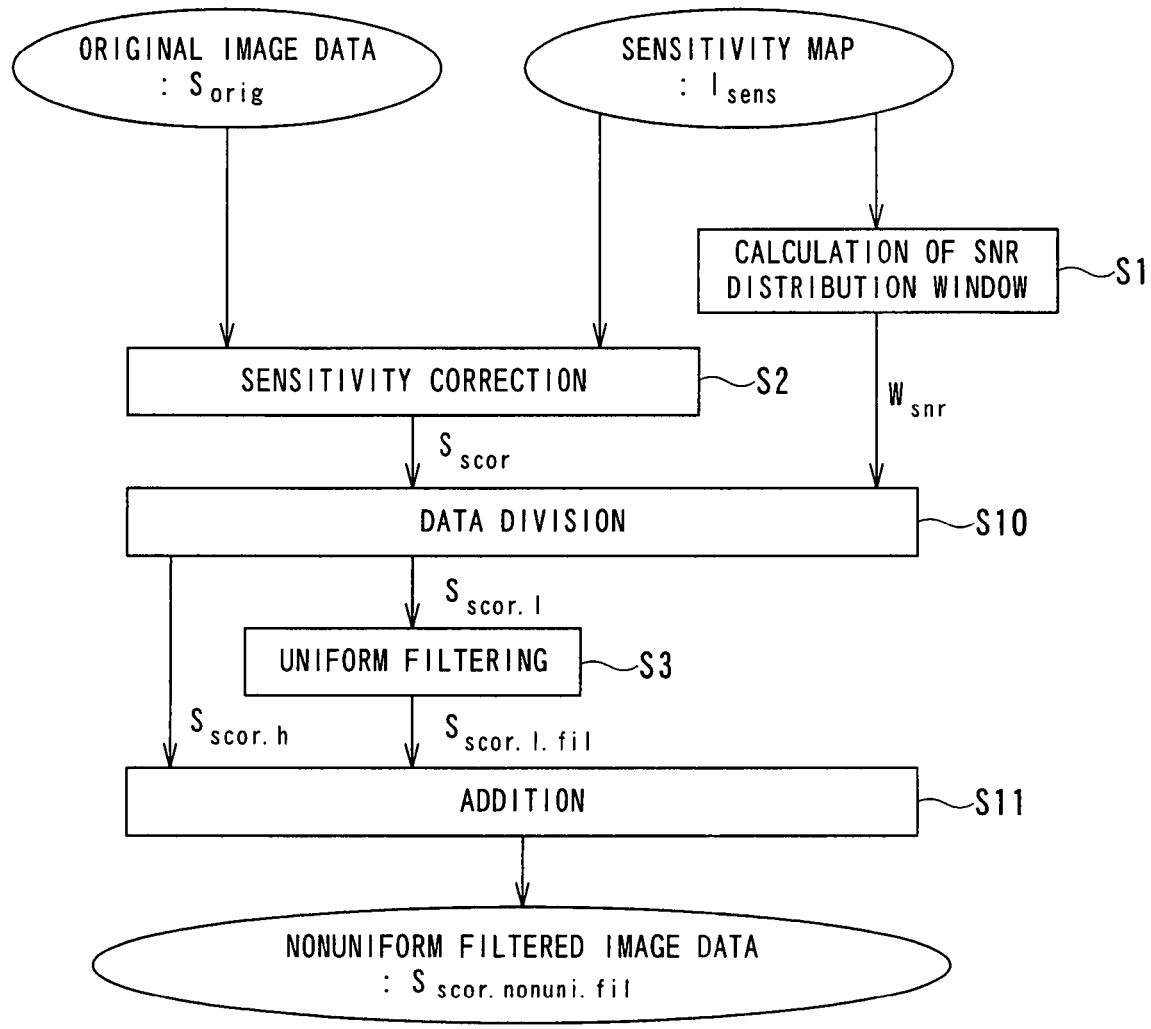
FIG. 4 is a flowchart showing a procedure of performing sensitivity correction to image data acquired from the image diagnostic apparatus with keeping an SNR distribution uniform by the data correction apparatus shown in FIG. 3.

FIG. 4 is a flowchart showing a procedure of performing sensitivity correction to image data acquired from the image diagnostic apparatus 6 with keeping an SNR distribution uniform by the data correction apparatus 1A shown in FIG. 3. The symbols including S with a number in FIG. 4 indicate each step of the flowchart. Note that the same number is attached to each step equivalent to that of the flowchart shown in FIG. 2 and a detail description of the equivalent steps is omitted.

First of all, in Step S1, the SNR distribution acquisition unit 3 calculates the weighting function $W_{snr}$ on the basis of the sensitivity map $I_{sens}$ acquired from the sensitivity map storage unit 10 and supplies the thus obtained weighting function $W_{snr}$ to the data dividing unit 12. This weighting function $W_{snr}$ (x, y, z) can be obtained on the basis of various methods as described above. Then, the thus obtained weighting function $W_{snr}$ (x, y, z) is used in the data dividing unit 12 for dividing the data in accordance with the SNR distribution.

Next, in Step S2, the sensitivity correction unit 2 uses the sensitivity map $I_{sens}$ acquired from the sensitivity map storage unit 10 to perform the sensitivity correction on the original image data $S_{orig}$ acquired from the image data storage unit 9, thereby obtaining the sensitivity correction image data $S_{scor}$. Then, the sensitivity correction unit 2 supplies the thus obtained sensitivity correction image data $S_{scor}$ to the data dividing unit 12.

The sensitivity correction image data $S_{scor}$ (x, y, z) can be generated on the basis of Expression (8).

$$S_{scor}(x,y,z) = S_{orig}(x,y,z)/I_{sens}(x,y,z) \tag{8}$$

Next, in Step S10, the data dividing unit 12 uses the weighting function $W_{snr}$ acquired from the SNR distribution acquisition unit 3 to divide the sensitivity correction image data $S_{scor}$ received from the sensitivity correction unit 2 into plural pieces of the sensitivity correction image component data in accordance with the size of the SNR. Then, the data dividing unit 12 supplies the sensitivity correction image component data $S_{scor.h}$ having the large SNR to the addition unit 13 and supplies on the other hand the sensitivity correction image component data $S_{scor.l}$ having the small SNR to the filter unit 4.

The component division on the sensitivity correction image data $S_{scor}$ (x, y, z) through the windowing with use of the weighting function $W_{snr}$ (x, y, z) can be conducted on the basis of Expression (9-1) and Expression (9-2). According to Expression (9-1) and Expression (9-2), the sensitivity correction image data $S_{scor}$ (x, y, z) is divided into two data, the sensitivity correction image component data $S_{scor.h}$ (x, y, z) and the sensitivity correction image component data $S_{scor.l}$ (x, y, z)

$$S_{scor.h}(x,y,z) = S_{scor}(x,y,z) * W_{snr}(x,y,z) \tag{9-1}$$

$$S_{scor.l}(x,y,z) = S_{scor}(x,y,z) * \{1 - W_{snr}(x,y,z)\} \tag{9-2}$$

It should be noted that $S_{scor.h}$ (x, y, z) is the sensitivity correction image component data having the good SNR and $S_{scor.l}$ (x, y, z) is the sensitivity correction image component data having bad SNR.

Next, in Step S3, the filter unit 4 conducts the filter processing with use of the uniform filter on the sensitivity correction image component data $S_{scor.l}$ having the small SNR received from the data dividing unit 12 or the sensitivity component data obtained through the conversion of the sensitivity correction image component data $S_{scor.l}$, thereby generating the filter processing image component data $S_{scor.l.fil}$ or the filter processing component data.

That is, for example, the smoothing filter shown in Expression (10) is applied only to the sensitivity correction image component data $S_{scor.l}$ (x, y, z) having the bad SNR, thereby generating the filter processing image component data $S_{scor.l.fil}$ (x, y, z).

$$S_{scor.l.fil}(x,y,z)=H[S_{scor.l}(x,y,z)] \quad (10)$$

wherein H denotes a filter operator.

Then, the filter unit 4 supplies the obtained filter processing image component data $S_{scor.l.fil}$ or the filter processing image component data $S_{scor.l.fil}$ obtained through the conversion of the filter processing component data to the addition unit 13.

Next, in Step S11, the addition unit 13 adds the sensitivity correction image component data $S_{scor.h}$ having the large SNR received from the data dividing unit 12 and the film processing image component data $S_{scor.l.fil}$ received from the filter unit 4 for synthesis, thereby generating the nonuniformity filtered image data $S_{scor.nonuni.fil}$.

This synthesis processing can be conducted on the basis of Expression (11).

$$S_{scor.nonuni.fil}(x,y,z)=S_{scor.h}(x,y,z)+S_{scor.l.fil}(x,y,z) \quad (11)$$

That is, the sensitivity correction image component data $S_{scor.h}$ (x, y, z) having the good SNR and the filter processing image component data $S_{scor.l.fil}$ (x, y, z) having the bad SNR which is subjected to the filtering are synthesized to each other, thereby calculating the nonuniformity filtered image data $S_{scor.nonuni.fil}$ (x, y, z) as the final correction image.

Then, the nonuniformity filtered image data $S_{scor.nonuni.fil}$ is written to the image data storage unit 9 of the image diagnostic apparatus 6 and displayed on the display of the display unit 11.

In other words, the above-mentioned data correction apparatus 1A conducts the weighting division in accordance with the size of the SNR on the image space on the image data after the sensitivity correction, and pieces of the image data having the small SNR are subjected to filtering by the uniform filters at different intensities, thereby synthesizing the divided image data. If the kernel having the sufficiently small support size in the real space is used in the filtering on the basis of the uniform filters, processing including the filter processing and the weighting division on the data are approximately almost equivalent even when either of the filter processing and the weighting division is conducted first. Therefore, according to the data correction apparatus 1A, the same effects as those in the data correction apparatus 1 shown in FIG. 1 can be obtained.

Figure 5:
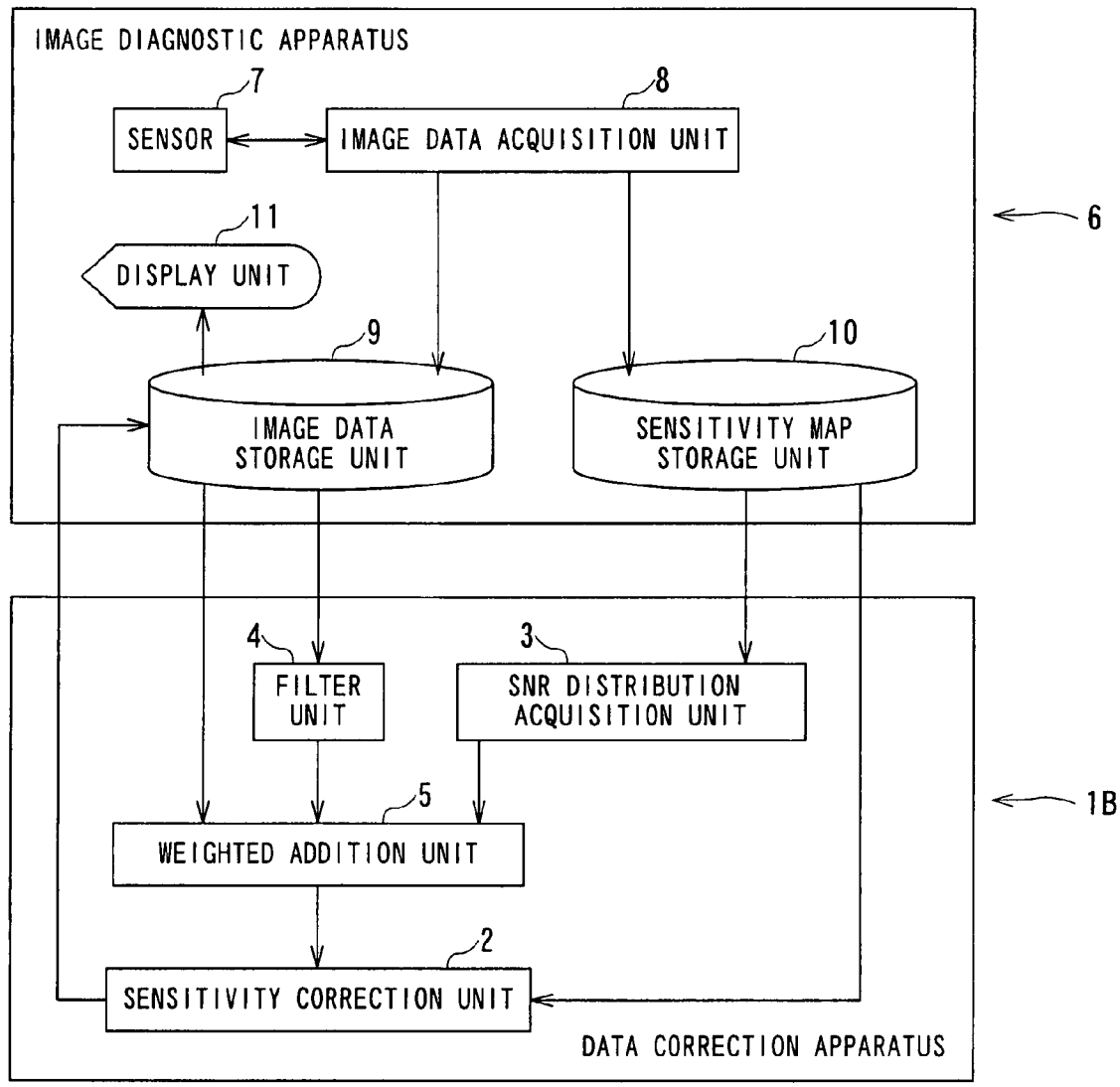
FIG. 5 is a functional block diagram showing a data correction apparatus according to a third embodiment of the present invention.

FIG. 5 is a functional block diagram showing a data correction apparatus according to a third embodiment of the present invention.

In the data correction apparatus 1B shown in FIG. 5, an order of processing is different from that of the data correction apparatus 1 shown in FIG. 1. Other constructions and operations of the data correction apparatus 1B are not different from those of the data correction apparatus 1 shown in FIG. 1 substantially. Therefore, same number is attached to a same component as that of the data correction apparatus 1 and explanation thereof is omitted.

The data correction apparatus 1B is provided with the sensitivity correction unit 2, the SNR distribution acquisition unit 3, the filter unit 4, and the weighted addition unit 5.

The filter unit 4 has a function of acquiring the original image data that is the target of the sensitivity correction from the image data storage unit 9, a function of performing the filter processing with use of the uniform filter on the original image data or the original data obtained through the conversion of the original image data to generate the filter processing original image data or the filter processing original data, and a function of supplying the thus generated filter processing original image data or the filter processing original image data obtained by way of the conversion of the filter processing original data to the weighted addition unit 5.

The weighted addition unit 5 has a function of performing the weighted addition on the original image data acquired from the image data storage unit 9 and the filter processing original image data received from the filter unit 4 on the basis of the SNR distribution information received from the SNR distribution acquisition unit 3 to generate the nonuniform filtered original image data and a function of supplying the thus generated nonuniform filtered original image data to the sensitivity correction unit 2.

The sensitivity correction unit 2 has a function of acquiring the sensitivity map used for the sensitivity correction from the sensitivity map storage unit 10 and using the acquired sensitivity map to perform the sensitivity correction on the nonuniform filtered original image data received from the weighted addition unit 5 to generate the nonuniformity filtered image data, and a function of writing the thus obtained nonuniformity filtered image data in the image data storage unit 9 of the image diagnostic apparatus 6.

Next, a description will be given of an operation and an action of the data correction apparatus 1B.

Figure 6:
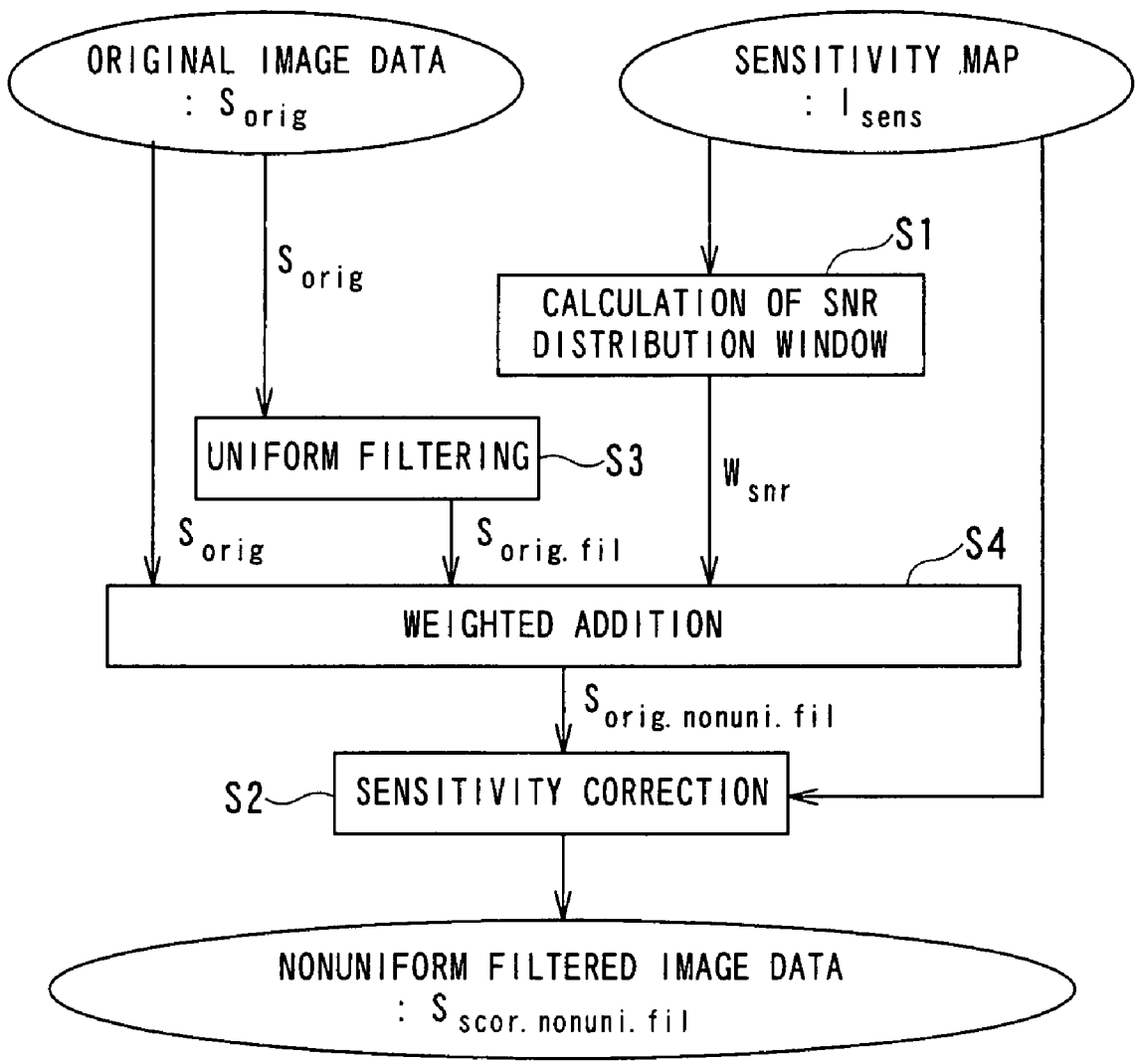
FIG. 6 is a flowchart showing a procedure of performing sensitivity correction to image data acquired from the image diagnostic apparatus with keeping an SNR distribution uniform by the data correction apparatus shown in FIG. 5.

FIG. 6 is a flowchart showing a procedure of performing sensitivity correction to image data acquired from the image diagnostic apparatus 6 with keeping an SNR distribution uniform by the data correction apparatus 1B shown in FIG. 5. The symbols including S with a number in FIG. 6 indicate each step of the flowchart. In FIG. 6, the same reference numerals will be given to steps equivalent to those in the flowchart shown in FIG. 2 and a description thereof will be given in brief. Therefore, the reference numbers do not match the order of the processing.

First of all, in Step S1, the SNR distribution acquisition unit 3 calculates the weighting function $W_{snr}$ on the basis of the sensitivity map $I_{sens}$ acquired from the sensitivity map storage unit 10 and supplies the thus obtained weighting function $W_{snr}$ to the weighted addition unit 5.

Next, in Step S3, the filter unit 4 acquires the original image data $S_{orig}$ that is the target of the sensitivity correction from the image data storage unit 9 and conducts the filter processing with use of the uniform filter on the acquired original image data $S_{orig}$ or the original data obtained through the conversion of the original image data $S_{orig}$, thereby generating the filtered original image data $S_{orig.fil}$ or the filtered original data.

That is, for example, as shown in Expression (12), the smoothing filter is applied to the entirety of the original image data $S_{orig}$ (x, y, z), thereby generating the filtered original image data $S_{orig.fil}$ (x, y, z).

$$S_{orig.fil}(x,y,z)=H[S_{orig}(x,y,z)] \quad (12)$$

wherein H denotes a filter operator.

Then, the filter unit 4 supplies the filtered original image data $S_{orig.fil}$ or the filtered original image data $S_{orig.fil}$ obtained by way of the conversion of the filtered original data to the weighted addition unit 5.

Next, in Step S4, the weighted addition unit 5 uses the weighting function $W_{snr}$ received from the SNR distribution acquisition unit 3 to perform the weighted addition of the original image data $S_{orig}$ acquired from the image data storage unit 9 and the filtered original image data $S_{orig.fil}$ received from the filter unit 4 for synthesis, thereby generating the nonuniform filtered original image data $S_{orig.nonfil.fil}$.

That is, first of all, as shown in Expression (13-1) and Expression (13-2), the weighting function $W_{snr}$ (x, y, z) is used to generate the component $S_{orig.h}$ (x, y, z) having good SNR from the original image data $S_{orig}$ (x, y, z), and the filtered component $S_{orig.l.fil}$ (x, y, z) having bad SNR using the filtered original image data $S_{orig.fil}$ (x, y, z) is generated. That is, the weight is applied on the filtered original image data $S_{orig.fil}$ (x, y, z) which is filtered to generate the component $S_{orig.l.fil}$ (x, y, z) having bad SNR.

$$S_{orig.h}(x,y,z) = W_{snr}(x,y,z) * S_{orig}(x,y,z) \quad (13\text{-}1)$$

$$S_{orig.l.fil}(x,y,z) = \{1 - W_{snr}(x,y,z)\} * S_{orig.fil}(x,y,z) \quad (13\text{-}2)$$

Next, as shown in Expression (14), the two components $S_{orig.h}$ (x, y, z) and $S_{orig.l.fil}$ (x, y, z) are synthesized, thereby obtain the nonuniform filtered original image data $S_{orig.nonfil.fil}$ (x, y, z) as the correction image with regard to SNR.

$$S_{orig.nonuni.fil}(x,y,z) = S_{orig.h}(x,y,z) + S_{orig.l.fil}(x,y,z) \quad (14)$$

In this way, the weighting is conducted on the component having good SNR and the filtered component having bad SNR for synthesis, thereby generating the nonuniform filtered original image data $S_{orig.nonuni.fil}$. Then, the weighted addition unit 5 supplies the thus generated nonuniform filtered original image data $S_{orig.nonfil.fil}$ to the sensitivity correction unit 2.

Next, in Step S1, the sensitivity correction unit 2 conducts the sensitivity correction on the nonuniform filtered original image data $S_{orig.nonfil.fil}$ received from the weighted addition unit 5 with use of the sensitivity map $I_{sens}$ acquired from the sensitivity map storage unit 10, thereby obtaining the nonuniformity filtered image data $S_{scor.nonuni.fil}$.

As shown in Expression (15), the sensitivity correction is conducted with use of the sensitivity map $I_{sens}$ (x, y, z), the image after the sensitivity correction subjected to the nonuniform SNR correction filter processing, that is, the nonuniformity filtered image data $S_{scor.nonuni.fil}$ is calculated on the basis of the nonuniform filtered original image data $S_{orig.nonfil.fil}$ (x, y, z).

$$S_{scor.nonuni.fil}(x,y,z) = S_{orig.nonuni.fil}(x,y,z) / I_{sens}(x,y,z) \quad (15)$$

Then, the sensitivity correction unit 2 writes the nonuniformity filtered image data $S_{scor.nonuni.fil}$ to the image data storage unit 9 of the image diagnostic apparatus 6. After that, the display unit 11 displays on the display the nonuniformity filtered image data $S_{scor.nonuni.fil}$ read out from the image data storage unit 9.

In other words, the above-mentioned data correction apparatus 1B is adapted to conduct the sensitivity correction after the filter processing at different intensities and the weighted addition to the image data. In this manner, the SNR is not changed even if the filter processing and the weighted addition are conducted on the image data before the correction and the sensitivity correction is finally conducted. Therefore, according to the data correction apparatus 1B, it is possible to obtain the same effects as those in the data correction apparatus 1 shown in FIG. 1.

Figure 7:
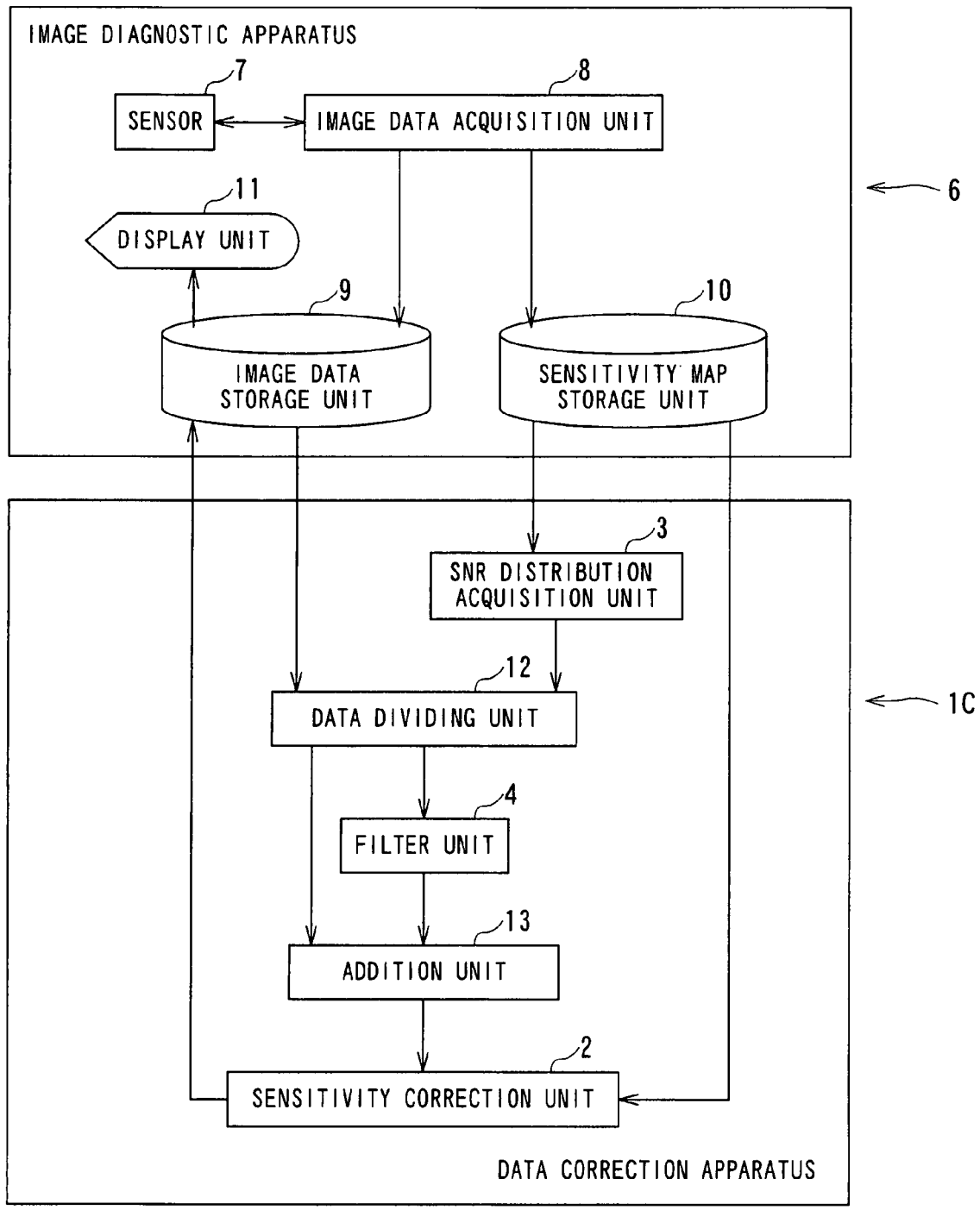
FIG. 7 is a functional block diagram showing a data correction apparatus according to a fourth embodiment of the present invention.

FIG. 7 is a functional block diagram showing a data correction apparatus according to a fourth embodiment of the present invention.

In the data correction apparatus 1C shown in FIG. 7, an order of processing is different from that of the data correction apparatus 1A shown in FIG. 3. Other constructions and operations of the data correction apparatus 1C are not different from those of the data correction apparatus 1A shown in FIG. 3 substantially. Therefore, same number is attached to a same component as that of the data correction apparatus 1A and explanation thereof is omitted.

Specifically, the data correction apparatus 1C is provided with the sensitivity correction unit 2, the SNR distribution acquisition unit 3, the filter unit 4, the data dividing unit 12, and the addition unit 13.

The data dividing unit 12 has a function of generating plural pieced of the original image component data in accordance with the size of the SNR from the original image data acquired from the image data storage unit 9 on the basis of the distribution information on the SNR acquired from the SNR distribution acquisition unit 3 and a function of supplying the original image component data with the small SNR to the filter unit 4 and supplying the original image component data with the large SNR to the addition unit 13.

Then, the filter unit 4 is configured to generate the filtered original image component data by performing the filter processing with the uniform filter and necessary transforms to the original image component data or the original component data obtained through the conversion of the original image component data, the addition unit 13 is configured to generate the nonuniform filtered original image data through the addition processing on the filtered original image component data and the original image component data having the large SNR. Furthermore, the sensitivity correction unit 2 is configured to write the nonuniformity filtered image data obtained by performing the sensitivity correction on the nonuniform filtered original image data, to the image data storage unit 9 of the image diagnostic apparatus 6.

Next, a description will be given of an operation and an action of the data correction apparatus 1C.

Figure 8:
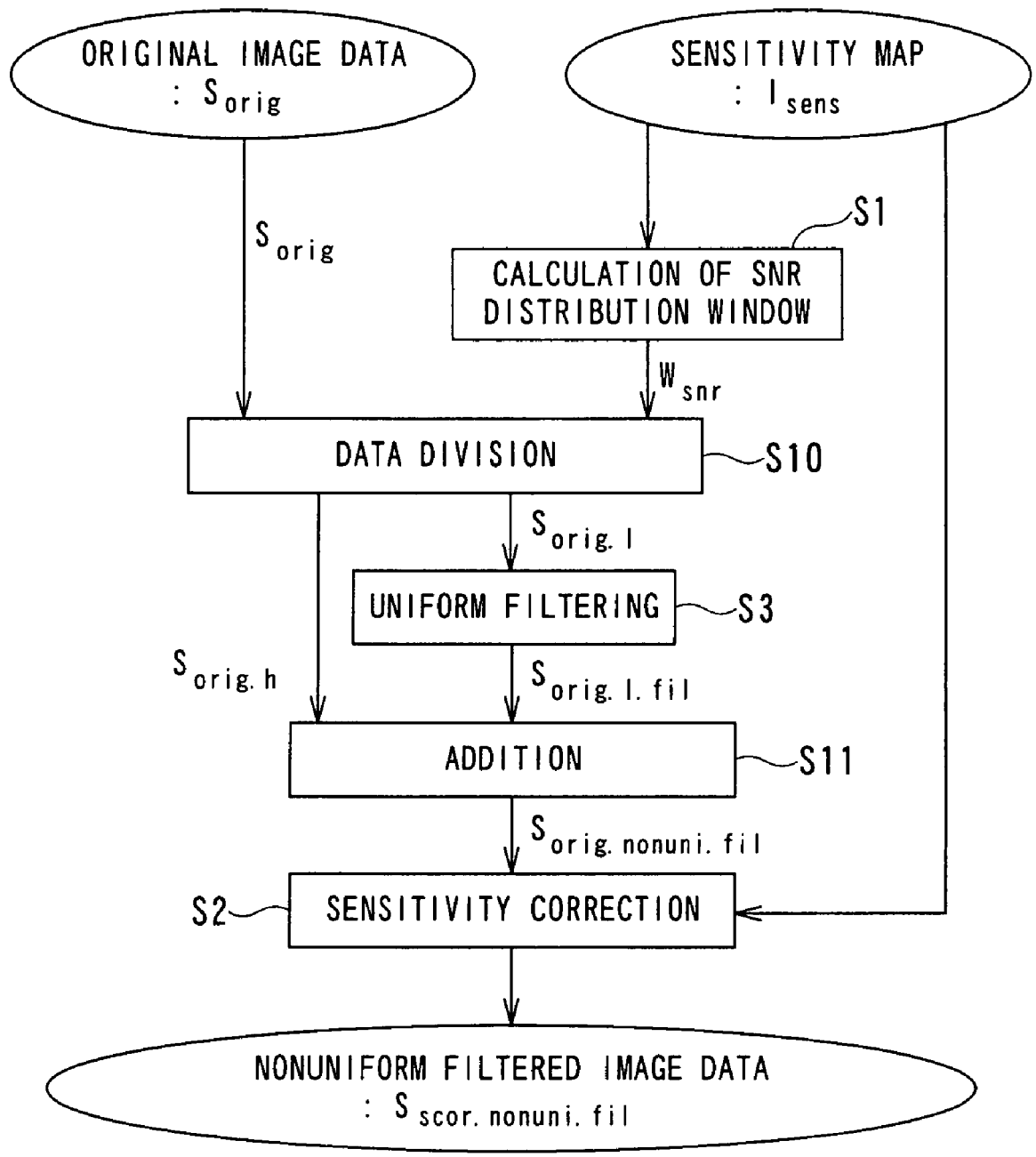
FIG. 8 is a flowchart showing a procedure of performing sensitivity correction to image data acquired from the image diagnostic apparatus with keeping an SNR distribution uniform by the data correction apparatus shown in FIG. 7.

FIG. 8 is a flowchart showing a procedure of performing sensitivity correction to image data acquired from the image diagnostic apparatus 6 with keeping an SNR distribution uniform by the data correction apparatus 1C shown in FIG. 7. The symbols including S with a number in FIG. 8 indicate each step of the flowchart. In FIG. 8, the same reference numerals will be given to steps equivalent to those in the flowchart shown in FIG. 4 and a description thereof will be given in brief. Therefore, the reference numbers do not match the order of the processing.

First of all, in Step S1, the SNR distribution acquisition unit 3 calculates the weighting function $W_{snr}$ on the basis of the sensitivity map $I_{sens}$ acquired from the sensitivity map storage unit 10 and supplies the thus obtained weighting function $W_{snr}$ to the data dividing unit 12.

Next, in Step S10, the data dividing unit 12 uses the weighting function $W_{snr}$ acquired from the SNR distribution acquisition unit 3 to divide the original image data $S_{orig}$ acquired from the image data storage unit 9 into the plural pieces of the original image component data in accordance with the size of the SNR.

The component division of the original image data $S_{orig}$ (x, y, z) through windowing with use of the weighting function $W_{snr}$ (x, y, z) is conducted as shown in Expression (16-1) and Expression (16-2). Then, the original image data $S_{orig}$ (x, y, z) is divided into two components of the original image component data $S_{orig.h}$ (x, y, z) which is a component having the large SNR and the original image component data $S_{orig.l}$ (x, y, z) which is a component having small SNR.

$$S_{orig.h}(x,y,z)=S_{orig}(x,y,z)*W_{snr}(x,y,z) \quad (16\text{-}1)$$

$$S_{orig.l}(x,y,z)=S_{orig}(x,y,z)*\{1-W_{snr}(x,y,z)\} \quad (16\text{-}2)$$

Then, the data dividing unit 12 supplies the original image component data $S_{orig.h}$ which is the component having large SNR to the addition unit 13 and on the other hand supplies the original image component data $S_{orig.l}$ which is the component having small SNR to the filter unit 4.

Next, in Step S3, the filter unit 4 conducts the filter processing with use of the uniform filter on the original image component data $S_{orig.l}$ having small SNR received from the data dividing unit 12 or the original component data obtained through the conversion of the original image component data $S_{orig.l}$, thereby generating the filtered original image component data $S_{orig.l.fil}$ or the filtered original component data.

That is, for instance, as shown in Expression (17), the smoothing filter is applied only to the original image component data $S_{orig.l}$ (x, y, z) having bad SNR, thereby obtaining the filtered original image component data $S_{orig.l.fil}$.

$$S_{orig.l.fil}(x,y,z)=H[S_{orig.l}(x,y,z)] \quad (17)$$

wherein H denotes a filter operator.

Then, the filter unit 4 supplies the thus obtained filtered original image component data $S_{orig.l.fil}$ or the filtered original image component data $S_{orig.l.fil}$ obtained through the conversion of the filtered original component data to the addition unit 13.

Next, in Step S11, the addition unit 13 adds the original image component data $S_{orig.h}$ having large SNR received from the data dividing unit 12 and the filtered original image component data $S_{orig.l.fil}$ received from the filter unit 4 for synthesis, thereby generating the nonuniform filtered original image data $S_{orig.nonuni.fil}$.

The synthesis processing between the original image component data $S_{orig.h}$ (x, y, z) having large SNR and the filtered original image component data $S_{orig.l.fil}$ (x, y, z) is conducted on the basis of Expression (18). Then, the nonuniform filtered original image data $S_{orig.nonuni.fil}$ (x, y, z) in which the weighting synthesis is conducted on the component having good SNR and the filtered component having bad SNR is obtained as the correction image with regard to the SNR through this synthesis processing.

$$S_{orig.nonuni.fil}(x,y,z)=S_{orig.h}(x,y,z)+S_{orig.l.fil}(x,y,z) \quad (18)$$

Then, the addition unit 13 supplies the nonuniform filtered original image data $S_{orig.nonuni.fil}$ to the sensitivity correction unit 2.

Next, in Step S2, the sensitivity correction unit 2 uses the sensitivity map $I_{sens}$ acquired from the sensitivity map storage unit 10 to conduct the sensitivity correction on the nonuniform filtered original image data $S_{orig.nonuni.fil}$ received from the addition unit 13, thereby obtaining the nonuniformity filtered image data $S_{scor.nonuni.fil}$.

This sensitivity correction is conducted on the basis of Expression (19), and the nonuniformity filtered image data $S_{scor.nonuni.fil}$ (x, y, z) that is an image subjected to the sensitivity correction and the nonuniform SNR correction filter processing from the nonuniform filtered original image data $S_{orig.nonuni.fil}$ (x, y, z) with use of the sensitivity map $I_{sens}$ (x, y, z) is calculated.

$$S_{scor.nonuni.fil}(x,y,z)=S_{orig.nonuni.fil}(x,y,z)/I_{sens}(x,y,z) \quad (19)$$

Then, the thus obtained nonuniformity filtered image data $S_{scor.nonuni.fil}$ is written to the image data storage unit 9 of the image diagnostic apparatus 6 and displayed on the display of the display unit 11.

In other words, the above-mentioned data correction apparatus 1C is adapted to conduct the sensitivity correction after the weighting division on the image data, the filter processing at different intensities and the addition synthesis. As described above, the SNR is not changed even when the filter processing and the weighting processing are conducted on the image data before the correction and lastly the sensitivity correction is conducted. Therefore, according to the data correction apparatus 1C, the same effects as those in the data correction apparatus 1A shown in FIG. 3 can be obtained.

As in the data correction apparatus 1, 1A, 1B, and 1C in the above-mentioned embodiments, the order of the three processing that are the sensitivity correction, the filter processing with the uniform filter and the weighting processing can be arbitrarily changed.

It should be noted that from the viewpoint of simplification in the filter processing, the filtering with the uniform filter may be preferably performed before the sensitivity correction in some cases. In view of the above, a description will be given of a calculation example of the filter function in the case where Wiener filter in which data on the FREBAS space is set as a target is used as the uniform filter.

The generated three-dimensional FREBAS space (X, Y, Z) is a space where the real space (x, y, z) is almost completely preserved. Therefore, when the Wiener filter is used, the power of noise is not set constant, and the power Pn of noise is treated as the function of the FREBAS space (X, Y, Z). The filtering with the Wiener filter may be conducted either before or after the sensitivity correction, but the power Pn of noise is preferably set to constant in terms of the filter processing. In view of the above, the filtering with use of the Wiener filter is conducted before the sensitivity correction and it is possible to deal with the power Pn of noise to be set constant.

That is, when the filtering with use of the Wiener filter is conducted before the sensitivity correction, as shown in Expression (20), the filter function WF (X, Y, Z) of the Wiener filter can be determined on the basis of the signal intensity Ps (X, Y, Z) of the image data in the FREBAS space (X, Y, Z) and the power Pn of noise.

$$WF(X,Y,Z)=Ps(X,Y,Z)/\{Ps(X,Y,Z)+Pn\} \quad (20)$$

On the other hand, when the filtering with use of the Wiener filter is conducted before the sensitivity correction, the power Pn of noise changes spatially, the power Pn=Pn (X, Y, Z) of noise is established and the filter function WF (X, Y, Z) is determined as shown in Expression (21).

$$WF(X,Y,Z)=Ps(X,Y,Z)/\{Ps(X,Y,Z)+Pn(X,Y,Z)\} \quad (21)$$

The power Pn (X, Y, Z) of noise can be obtained on the basis of Expression (22-1) and Expression (22-2) using the weighting function W (x, y, z) that is equivalent to an inverse number of the sensitivity distribution.

$$W(X,Y,Z)=FR[W(x,y,z)] \quad (22\text{-}1)$$

$$Pn(X,Y,Z)=W(X,Y,Z)*Pn' \quad (22\text{-}2)$$

wherein FR[ ] denotes FREBAS transform and Pn' denotes power of noise at end of FREBAS space (or k-space). That is, the power Pn (X, Y, Z) of noise of Expression (21) can be obtained on the basis of the weighting function W (X, Y, Z) obtained through the FREBAS transform of the weighting function W (x, y, z) and the power Pn' of noise at an end part of the FREBAS space (or the k-space).

Incidentally, as described above, the data correction apparatus 1, 1A, 1B, or 1C can be added to or built in the biological information measuring device or the image diagnostic apparatus. In view of the above, as a specific example, a description will be made of the sensitivity correction processing to an image obtained while the data correction apparatus 1A shown in FIG. 3 is built in the MRI apparatus and the multi coil is set as the sensor.

Figure 9:
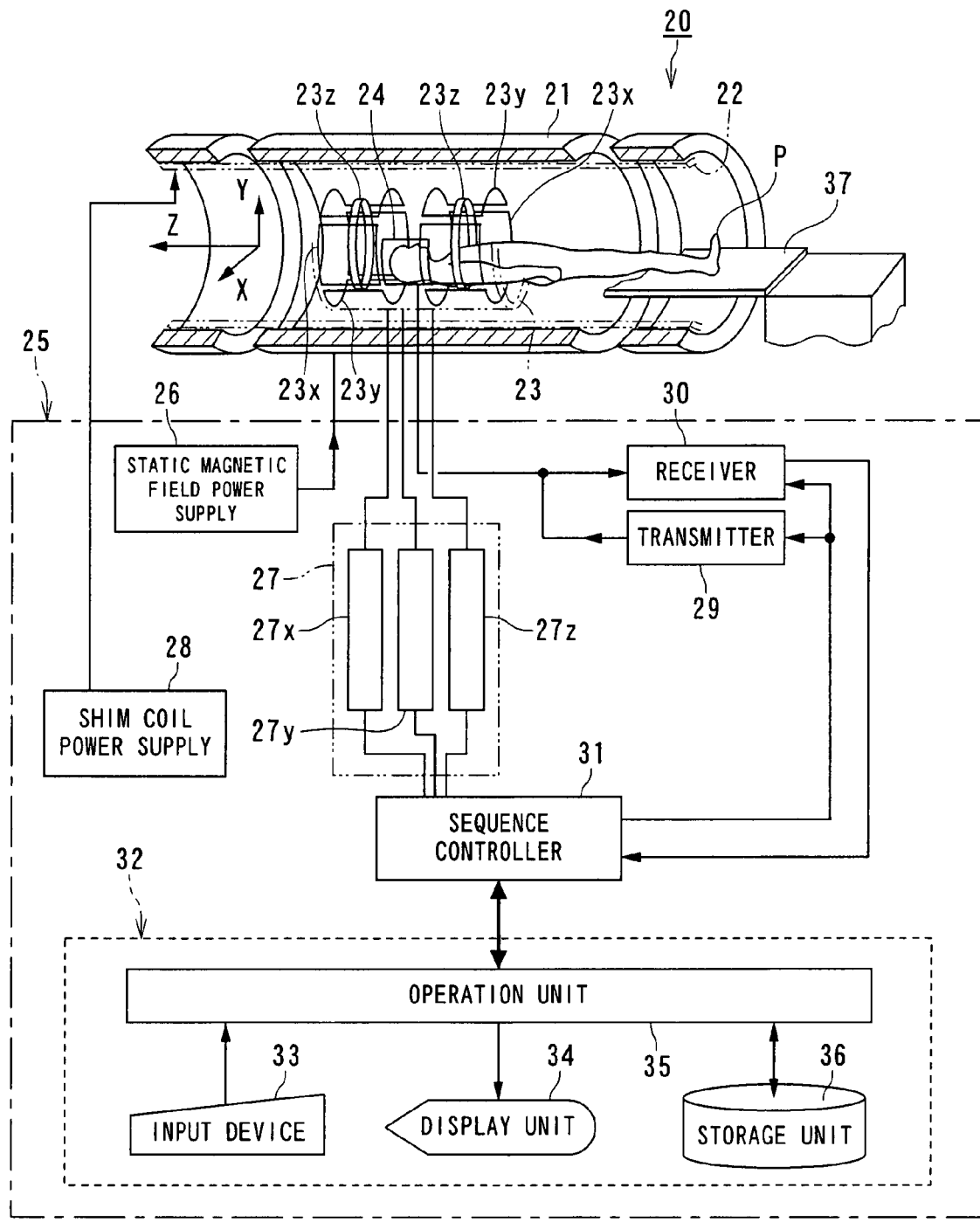
FIG. 9 is a structure diagram showing a magnetic resonance imaging apparatus according to an embodiment of the present invention.

FIG. 9 is a structure diagram showing a magnetic resonance imaging apparatus according to an embodiment of the present invention.

A magnetic resonance imaging apparatus 20 includes a static field magnet 21 for generating a static magnetic field, a shim coil 22 arranged inside the static field magnet 21 which is cylinder-shaped, a gradient coil unit 23 and a RF coil 24. The static field magnet 21, the shim coil 22, the gradient coil unit 23 and the RF coil 24 are built in a gantry (not shown).

The magnetic resonance imaging apparatus 20 also includes a control system 25. The control system 25 includes a static magnetic field power supply 26, a gradient power supply 27, a shim coil power supply 28, a transmitter 29, a receiver 30, a sequence controller 31 and a computer 32. The gradient power supply 27 of the control system 25 includes an X-axis gradient power supply 27x, a Y-axis gradient power supply 27y and a Z-axis gradient power supply 27z. The computer 32 includes an input device 33, a monitor 34, an operation unit 35 and a storage unit 36.

The static field magnet 21 communicates with the static magnetic field power supply 26. The static magnetic field power supply 26 supplies electric current to the static field magnet 21 to get the function to generate a static magnetic field in an imaging region. The static field magnet 21 includes a superconductivity coil in many cases. The static field magnet 21 gets current from the static magnetic field power supply 26 which communicates with the static field magnet 21 at excitation. However, once excitation has been made, the static field magnet 21 is usually isolated from the static magnetic field power supply 26. The static field magnet 21 may include a permanent magnet which makes the static magnetic field power supply 26 unnecessary.

The static field magnet 21 has the cylinder-shaped shim coil 22 coaxially inside itself. The shim coil 22 communicates with the shim coil power supply 28. The shim coil power supply 28 supplies current to the shim coil 22 so that the static magnetic field becomes uniform.

The gradient coil unit 23 includes an X-axis gradient coil unit 23x, a Y-axis gradient coil unit 23y and a Z-axis gradient coil unit 23z. Each of the X-axis gradient coil unit 23x, the Y-axis gradient coil unit 23y and the Z-axis gradient coil unit 23z which is cylinder-shaped is arranged inside the static field magnet 21. The gradient coil unit 23 has also a bed 37 in the area formed inside it which is an imaging area. The bed 37 supports an object P. Around the bed 37 or the object P, the RF coil 24 may be arranged instead of being built in the gantry.

The gradient coil unit 23 communicates with the gradient power supply 27. The X-axis gradient coil unit 23x, the Y-axis gradient coil unit 23y and the Z-axis gradient coil unit 23z of the gradient coil unit 23 communicate with the X-axis gradient power supply 27x, the Y-axis gradient power supply 27y and the Z-axis gradient power supply 27z of the gradient power supply 27 respectively.

The X-axis gradient power supply 27x, the Y-axis gradient power supply 27y and the Z-axis gradient power supply 27z supply currents to the X-axis gradient coil unit 23x, the Y-axis gradient coil unit 23y and the Z-axis gradient coil unit 23z respectively so as to generate gradient magnetic fields Gx, Gy and Gz in the X, Y and Z directions in the imaging area.

The RF coil 24 communicates with the transmitter 29 and the receiver 30. The RF coil 24 has a function to transmit a radio frequency signal given from the transmitter 29 to the object P and receive an NMR signal generated due to an nuclear spin inside the object P which is excited by the radio frequency signal to give to the receiver 30.

Figure 10:
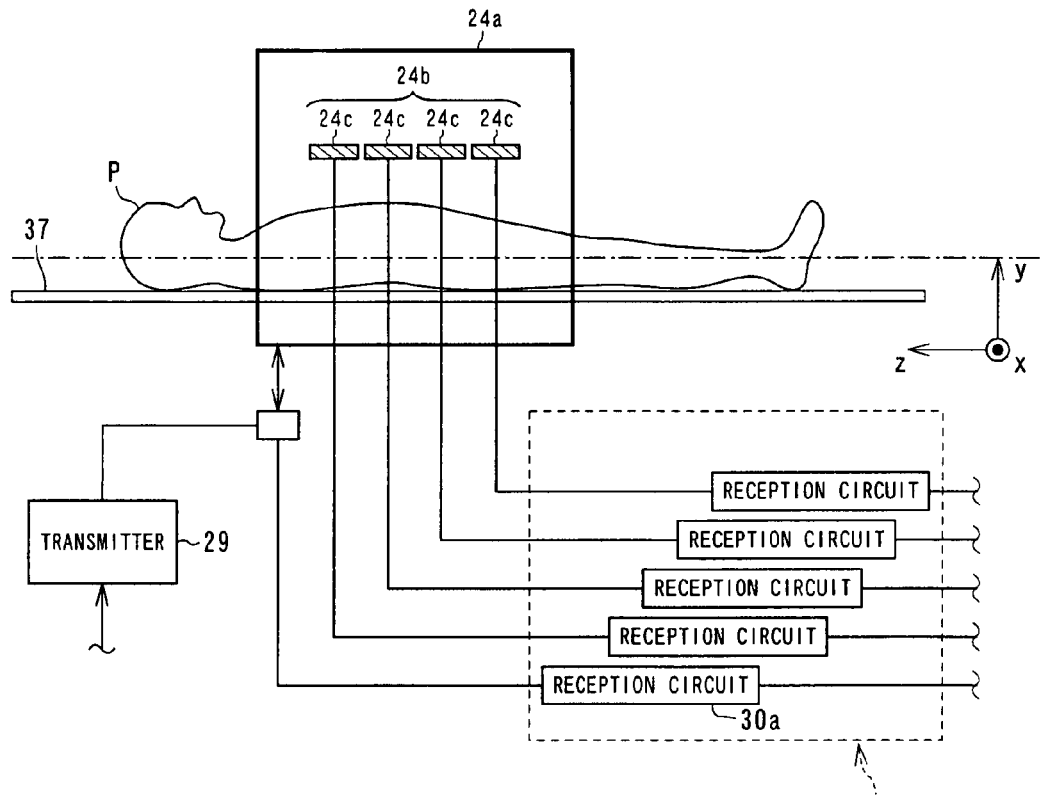
FIG. 10 is a diagram showing an example of detail structure of the RF coil shown in FIG. 9.
Figure 11:
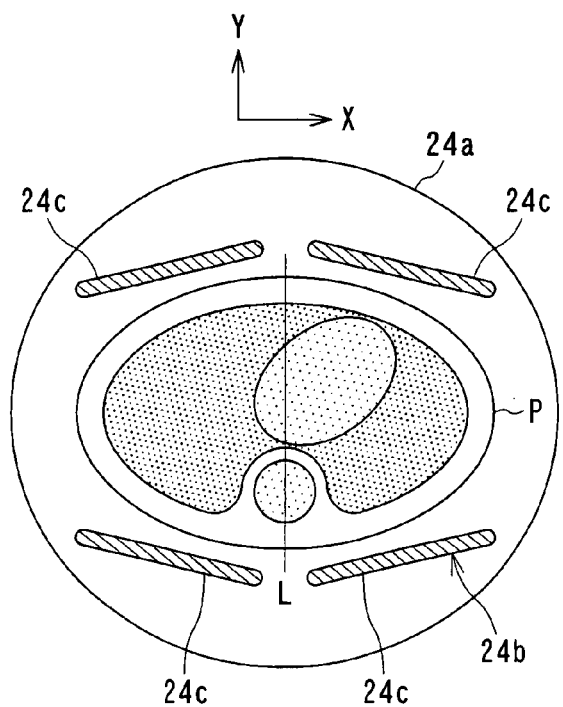
FIG. 11 is a sectional illustration showing an example arrangement of the WB coil and the phased array coils shown in FIG. 10.

FIG. 10 is a diagram showing an example of detail structure of the RF coil 24 shown in FIG. 9. FIG. 11 is a sectional illustration showing an example arrangement of the WB coil 24a and the phased array coils 24b shown in FIG. 10.

The RF coil 24 is structured by a transmission RF coil 24 and a reception RF coil 24, for example. The transmission RF coil 24 uses a whole-body (WB) coil 24a while the reception RF coil 24 uses a phased array coil 24b. The phased array coil 24b has a plurality of surface coils 24c. The surface coils 24c are separately connected to respective reception circuits 30a.

Meanwhile, the surface coils 24c of the phased array coil 24b are arranged, symmetric about the Z-axis, in peripheral regions of a section L including a particular region of interest in the object P for example. Furthermore, the WB coil 24a is provided at the outer of the phased array coil 24b. Thus, a radio frequency signal can be transmitted to the object P by the WB coil 24a while an NMR signal of from the section L including the particular region of interest can be received at multi-channels by the WB coil 24a or the surface coils 24c of the phased array coil 24b and provided to the reception circuits 30a of the receiver 30.

However, the RF coil 24 may be structured by desired coils suited for various applications or by a single coil.

The sequence controller 31 of the control system 25 communicates with the gradient power supply 27, the transmitter 29 and the receiver 30. The sequence controller 31 has a function to storage sequence information describing control information needed in order to make the gradient power supply 27, the transmitter 29 and the receiver 30 drive and generate gradient magnetic fields Gx, Gy and Gz in the X, Y and Z directions and a radio frequency signal by driving the gradient power supply 27, the transmitter 29 and the receiver 30 according to a predetermined sequence stored. The control information above-described includes motion control information, such as intensity, impression period and impression timing of the pulse electric current which should be impressed to the gradient power supply 27

The sequence controller 31 is also configured to give raw data to the computer 32. The raw data is complex number data obtained through the detection of a NMR signal and A/D conversion to the NMR signal detected in the receiver 30.

The transmitter 29 has a function to give a radio frequency signal to the RF coil 24 in accordance with control information provided from the sequence controller 31. The receiver 30 has a function to generate raw data which is digitized complex number data by detecting a NMR signal given from the RF coil 24 and performing predetermined signal processing and A/D converting to the NMR signal detected. The receiver 30 also has a function to give the generated raw data to the sequence controller 31.

The computer 32 gets various functions and the data correction apparatus 1A is configured by the operation unit 35 executing some programs stored in the storage unit 36 of the computer 32. Parts corresponding to the computer 32 may include some specific circuits instead of using some of the programs.

Figure 12:
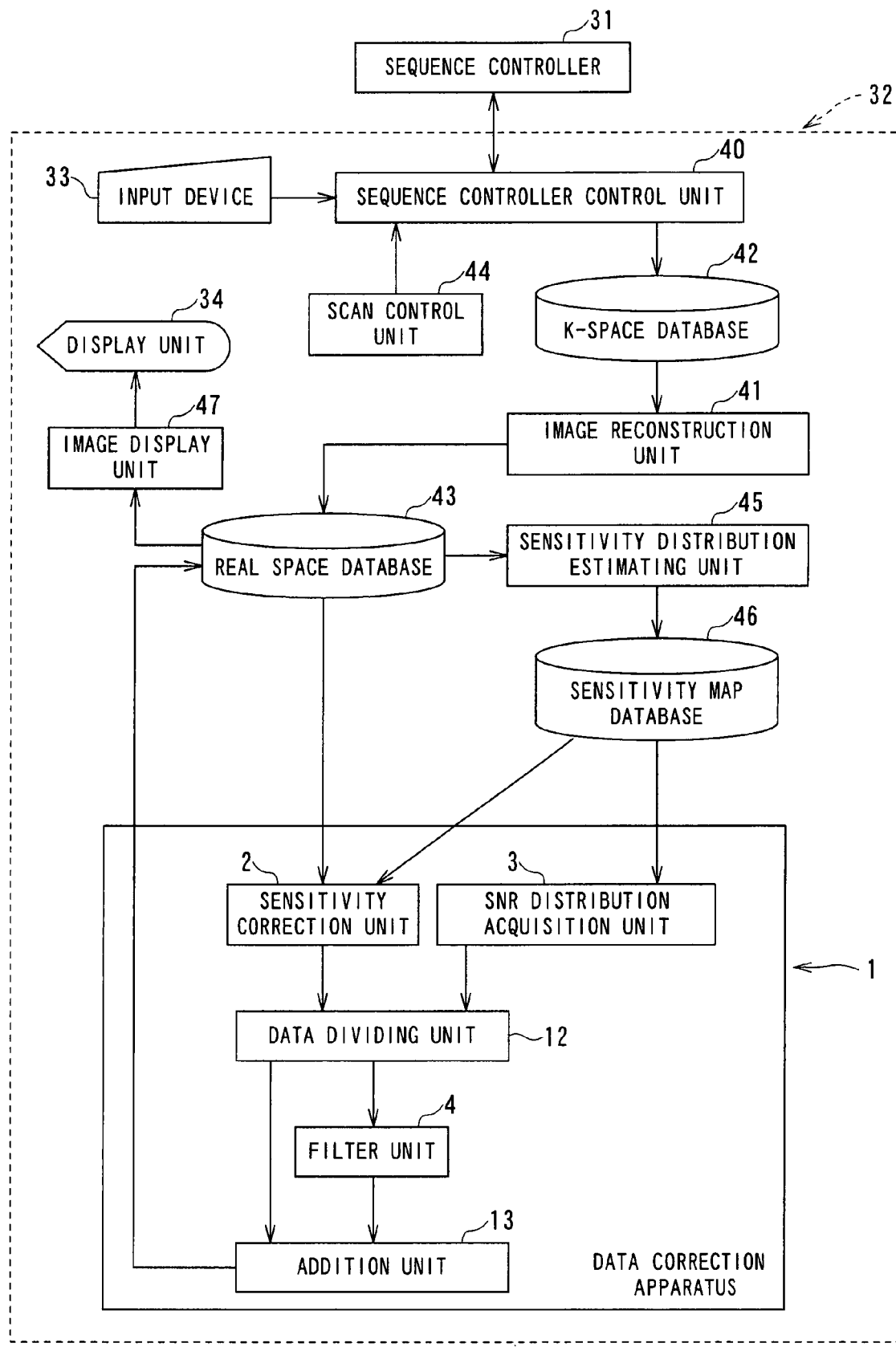
FIG. 12 is a functional block diagram of the computer shown in FIG. 1.

FIG. 12 is a functional block diagram of the computer 32 shown in FIG. 1.

The computer 32 with programs functions as a sequence controller control unit 40, an image reconstruction unit 41, a k-space database 42, a real space database 43, a scan control unit 44, a sensitivity distribution estimating unit 45, a sensitivity map database 46, an image display unit 47 and the data correction apparatus 1A.

The sequence controller control unit 40 has a function for controlling the driving of the sequence controller 31 by giving predetermined sequence information to the sequence controller 31 based on information from the input device 33 or another element. Further, the sequence controller control unit 40 has a function for receiving raw data from the sequence controller 31 and arranging the raw data to a k-space (Fourier space) formed in the k-space database 42. Therefore, the k-space database 42 stores the raw data generated by the receiver 30 as k-space data, and the k-space data are arranged to the k-space formed in the k-space database 42.

The image reconstruction unit 41 has a function for capturing the k-space data from the k-space database 42, performing predetermined signal processing, reconstructing real space data such as image data, and writing the real space data to the real space database 43. The image reconstruction unit 41 is configured to perform various processing such as two-dimensional or three-dimensional Fourier transform processing on the k-space data arranged in the k-space of the k-space database 42, thereby making it possible to reconstruct the real space image data and the real space data to be used for sensitivity estimation of the respective surface coils 24c from the k-space data. Therefore, the real space database 43 stores the real space data such as image data.

The sensitivity distribution estimating unit 45 has a function of reading out the real space data for the sensitivity estimation of the respective surface coils 24c from the real space database 43 to estimate the spatial and/or temporal sensitivity distribution of the respective surface coils 24c for synthesis and writing the resultant to the sensitivity map database 46 as the sensitivity map data. The estimation of the sensitivity distribution can be conducted on the basis of a known arbitrary method. An estimation method including performing the sensitivity pre-scan for the sensitivity distribution estimation and using the thus obtained real space data to estimate the sensitivity distribution is practical. For example, a method of obtaining the sensitivity distribution on the basis of a ratio between each intensity of the signals collected with use of the respective surface coils 24c and the corresponding intensity of the signals collected with use of the WB coil 24a in the sensitivity pre-scan, a method of obtaining the sensitivity distribution on the basis of each intensity of the signals collected with use of the respective surface coils 24c while adjusting the contrast, and the like are proposed.

Therefore, the sensitivity map database 46 stores the sensitivity map data indicating the sensitivity distributions corresponding to the respective surface coils 24c.

The scan control unit 44 has a function of supplying the sequence for the sensitivity pre-scan and the sequence for the main scan for the image collection to the sequence controller control unit 40, thereby executing the sensitivity pre-scan and the main scan.

The image display unit 47 has a function of reading the image data from the real space database 43 to be supplied to the display unit 34, thereby displaying the image data on the display unit 34.

The data correction apparatus 1A has the above-mentioned structure shown in FIG. 3 and a description thereof will be omitted. It should be noted that the data correction apparatus 1, 1B, or 1C having the structure shown in FIG. 1, 5, or 7 may be used.

Next, a description will be given of an operation and an action of the magnetic resonance imaging apparatus 20.

Figure 13:
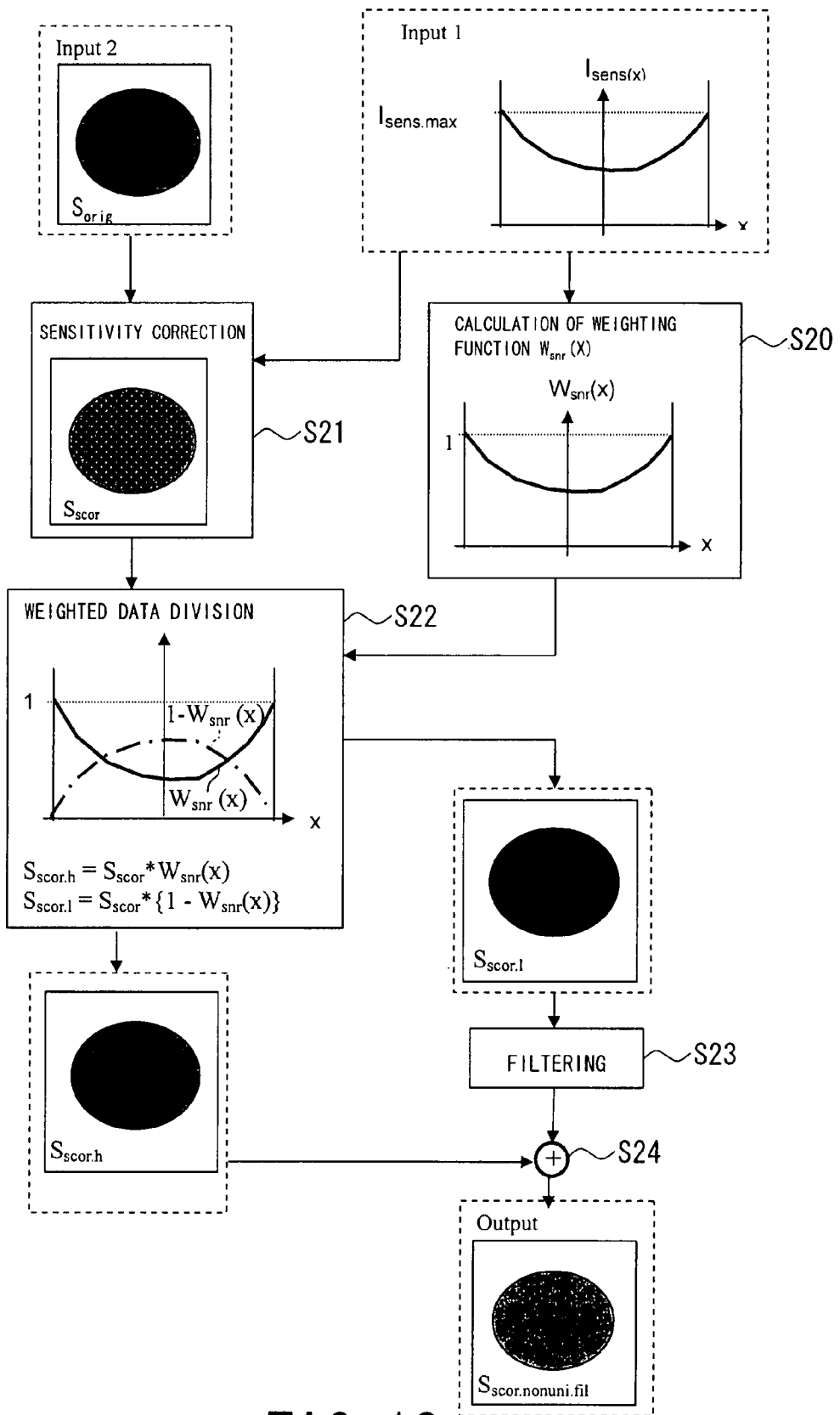
FIG. 13 is a flowchart showing a procedure of acquiring an image of the object and subsequently performing sensitivity correction regarding the respective surface coils to the acquired image data with keeping an SNR distribution uniform by the magnetic resonance imaging apparatus shown in FIG. 9.

FIG. 13 is a flowchart showing a procedure of acquiring an image of the object P and subsequently performing sensitivity correction regarding the respective surface coils 24c to the acquired image data with keeping an SNR distribution uniform by the magnetic resonance imaging apparatus 20 shown in FIG. 9. The symbols including S with a number in FIG. 13 indicate each step of the flowchart.

First of all, the sensitivity map data of the respective surface coils 24c is obtained. For that purpose, the scan control unit 44 supplies the sequence for the sensitivity pre-scan to the sequence controller control unit 40, the sequence for the sensitivity pre-scan is output from the sequence controller control unit 40 to the sequence controller 31. After that, the sequence controller 31 drives the gradient power supply 27, the transmitter 29, and the receiver 30 in accordance with the sequence for the sensitivity pre-scan, thereby forming the X-axis gradient power Gx, the Y-axis gradient power Gy, and the Z-axis gradient power Gz in the imaging area where the object P is set and also generating radio frequency signals.

Then, the NMR signals generated through the nuclear magnetic resonance inside the object P are received by the RF coil 24 and supplied to the receiver 30. The receiver 30 receives the NMR signals from the RF coil 24 and executes various signal processing including the A/D conversion, thereby generating raw data that is the NMR signals of the digital data. The receiver 30 supplies the thus generated raw data to the sequence controller 31. The sequence controller 31 supplies the raw data to the sequence controller control unit 40, and the sequence controller control unit 40 arranges the raw data in the k-space formed in the k-space database 42. Then, the image reconstruction unit 41 takes in the k-space data from the k-space database 42 and reconstructs the real space data for the sensitivity estimation of the respective surface coils 24c through the image reconstruction processing to be written to the real space database 43.

After that, the sensitivity distribution estimating unit 45 reads out the real space data for the sensitivity estimation of the respective surface coils 24c from the real space database 43, estimates the spatial and/or temporal sensitivity distribution of the respective surface coils 24c, for instance, through a processing such as low-pass filtering for synthesis, and writes the resultant as the sensitivity map data to the sensitivity map database 46. For simplicity of the description, when it is assumed that the sensitivity map data has the one-dimensional spatial distribution in the x direction, the sensitivity map data $I_{sens}(x)$ representing sensitivity distributions of the respective surface coils 24c shown in FIG. 13 is obtained as input data Input 1 to the data correction apparatus 1A.

Next, the main scan for the imaging is executed following the sensitivity pre-scan. For that purpose, the scan control unit 44 supplies the sequence for the main scan to the sequence controller control unit 40, the sequence for the main scan is output from the sequence controller control unit 40 to the sequence controller 31. After that, in a similar flow to the sensitivity pre-scan, the sequence controller 31 drives and controls the gradient power supply 27, the transmitter 29, and the receiver 30 in accordance with the sequence for the main scan, thereby collecting the raw data for the imaging. The collected raw data is arranged in the k-space formed in the k-space database 42 as the k-space data.

Then, the image reconstruction unit 41 takes in the k-space data for the imaging from the k-space database 42 to reconstruct the image data through the image reconstruction processing to be written to the real space database 43. This image data is under the influence of the sensitivity distribution in the x direction of the respective surface coils 24c as shown in Input 1, and it is therefore necessary to conduct the sensitivity correction. However, the power of noise before the sensitivity correction is constant, and if an attempt is made to set the sensitivity constant by conducting the sensitivity correction, the power of noise becomes non-uniform. In view of the above, it is necessary to conduct not only the sensitivity correction but also the correction of the non-uniform SNR. For that purpose, the original image data $S_{orig}$ before the sensitivity correction is input as Input 2 to the data correction apparatus 1A.

After that, in Step S20, the SNR distribution acquisition unit 3 of the data correction apparatus 1A normalizes the sensitivity map $I_{sens}$ (x) acquired from the sensitivity map database 46 as Input 1, for example, through Expression (23) with use of the maximum sensitivity $I_{sens.max}$ so that the maximum value becomes 1, thereby obtaining the weighting function $W_{snr}$ (x).

$$W_{snr}(x)=I_{sens}(x)/I_{sens.max} \tag{23}$$

This weighting function $W_{snr}$ (x) is used as the WINDOW function for dividing the image data obtained in the main scan for the imaging into two pieces in accordance with high SNR and low SNR. For that reason, the SNR distribution acquisition unit 3 supplies the thus obtained weighting function $W_{snr}$ (x) to the data dividing unit 12.

Next, in Step S21, the sensitivity correction unit 2 conducts the sensitivity correction on the original image data $S_{orig}$ acquired from the real space database 43 with the sensitivity map data $I_{sens}$ (x) acquired from the sensitivity map database 46, thereby obtaining the sensitivity correction image data $S_{scor}$. The sensitivity correction unit 2 supplies the thus obtained sensitivity correction image data $S_{scor}$ to the data dividing unit 12.

Next, in Step S22, the data dividing unit 12 uses the weighting function $W_{snr}$ (x) acquired from the SNR distribution acquisition unit 3 to determine a division function (Window function) for dividing the sensitivity correction image data $S_{scor}$ acquired from the sensitivity correction unit 2 into two components in accordance with high and low levels of the SNR. That is, when a division function for generating a component in which the SNR level is high is set as Wh (x) and a division function for generating a component in which the SNR level is low is set as Wl (x), the division functions Wh (x) and Wl (x) are determined with use of the weighting function $W_{snr}$ (x) as shown in Expression (24-1) and Expression (24-2).

$$Wh(x)=W_{snr}(x) \tag{24-1}$$

$$Wl(x)=1-W_{snr}(x) \tag{24-2}$$

Then, while the division function Wh (x) as represented by the solid line and the division function Wl (x) as represented by the dashed-dotted line are used through the calculations shown in Expression (25-1) and Expression (25-2), the sensitivity correction image data $S_{scor}$ is divided into two components of the sensitivity correction image component data $S_{scor.h}$ in which the SNR level is high and the sensitivity correction image component data $S_{scor.l}$ in which the SNR level is low.

$$S_{scor.h}=S_{scor}*Wh(x)=S_{scor}*W_{snr}(x) \tag{25-1}$$

$$S_{scor.l}=S_{scor}*Wl(x)=S_{scor}*\{1-W_{snr}(x)\} \tag{25-2}$$

Then, the data dividing unit 12 supplies, the sensitivity correction image component data $S_{scor.h}$ in which the SNR level is high to the addition unit 13 and on the other hand supplies the sensitivity correction image component data $S_{scor.l}$ in which the SNR level is low to the filter unit 4.

Next, in Step S23, the filter unit 4 applies a normal noise reduction filtering, which is used in the filter processing on the spatially uniform data, to the sensitivity correction image component data $S_{scor.l}$ in which the SNR level is low acquired from the data dividing unit 12. The noise reduction filter can be composed of any spatially uniform filter in a large sense in which the sensitivity map data $I_{sens}$ (x) is not utilized. For noise reduction filter, a uniform filter such as the linear filter, the wiener Filter, or the structure optimization filter may be used. The filter processing may be performed in the k-space. In that case, the sensitivity correction image component data $S_{scor.l}$ is once converted into the k-space data and then subjected to the filter processing. The k-space data after the filtering is converted into the real space data. Then, the filter unit 4 supplies the filtered image component data $S_{scor.l.fil}$ obtained through the filter processing to the addition unit 13.

Next, in Step S24, the addition unit 13 adds the sensitivity correction image component data $S_{scor.h}$ having large SNR received from the data dividing unit 12 and the filtered image component data $S_{scor.l.fil}$ received from the filter unit 4 for synthesis, thereby generating the nonuniformity filtered image data $S_{scor.nonuni.fil}$. This nonuniformity filtered image data $S_{scor.nonuni.fil}$ is image data obtained by generating an image component having low SNR to which filtering having a strong intensity is applied with the Window function and an image component to which filtering is not applied and subsequently performing the weighted addition synthesis so that the image component to which the filtering is applied has a larger weight. Therefore, as a result, this image data is equivalent to image data obtained while the filter processing different in noise reduction effects in accordance with the spatial nonuniformity of the SNR distribution are performed on the original image data $S_{orig}$.

Then, the non-uniformity filtered image data $S_{scor.nonuni.fil}$ is set as an output (Output) of the data correction apparatus 1A and is written to the real space database 43. After that, the image display unit 47 reads out from the real space database 43 the nonuniformity filtered image data $S_{scor.nonuni.fil}$ to be supplied to the display unit 34, thereby displaying the nonuniform filtered image on the display unit 34. As a result, the image on which the sensitivity correction and the SNR nonuniform distribution correction are performed is displayed on the display unit 34.

It should be noted that as described above, instead of the data correction apparatus 1A, the data correction apparatus 1 shown in FIG. 1, the data correction apparatus 1B shown in FIG. 5, or the data correction apparatus 1C shown in FIG. 7 may be built in the computer 32 of the magnetic resonance imaging apparatus 20.

In a case where the data correction apparatus 1 shown in FIG. 1 is built in the computer 32 of the magnetic resonance imaging apparatus 20, image data to which a filter is applied and image data to which no filter is applied are generated, and the image data to which the filter is applied with use of the Window function in accordance with degree of SNR and the image data to which no filter is applied are synthesized to each other so that the weight of the filtered image data is set larger as the component has lower SNR.

In addition, when the data correction apparatus 1B shown in FIG. 5 or the data correction apparatus 1C shown in FIG. 7 is built in the computer 32 of the magnetic resonance imaging apparatus 20 and the correction with regard to the nonuniform SNR is performed before the sensitivity correction, the spatial distribution of the noise is constant, and accordingly the sensitivity correction is performed after the filtering with setting the power of noise constant, which leads to ease in the processing.

(Simulation Experiment)

Next, a description will be given of a simulation result in which a correction is performed on an abdominal part image of the object obtained in the MRI apparatus by the data correction apparatus 1 shown in FIG. 1.

Figure 14:
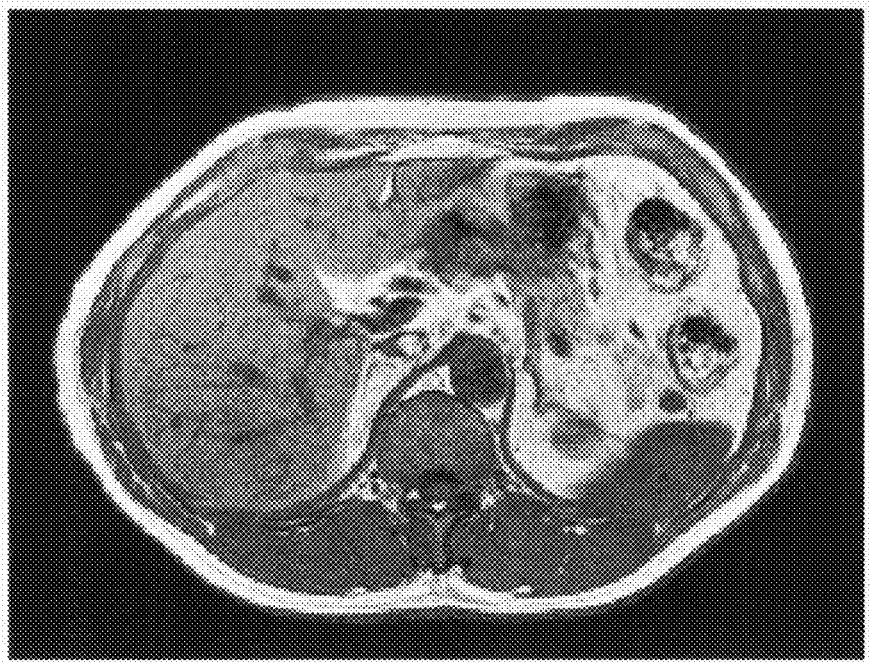
FIG. 14 shows an ideal abdominal image $S_{ideal\_scor}$ after sensitivity correction assumed on a simulation of image correction by the data correction apparatus shown in FIG. 1.
Figure 15:
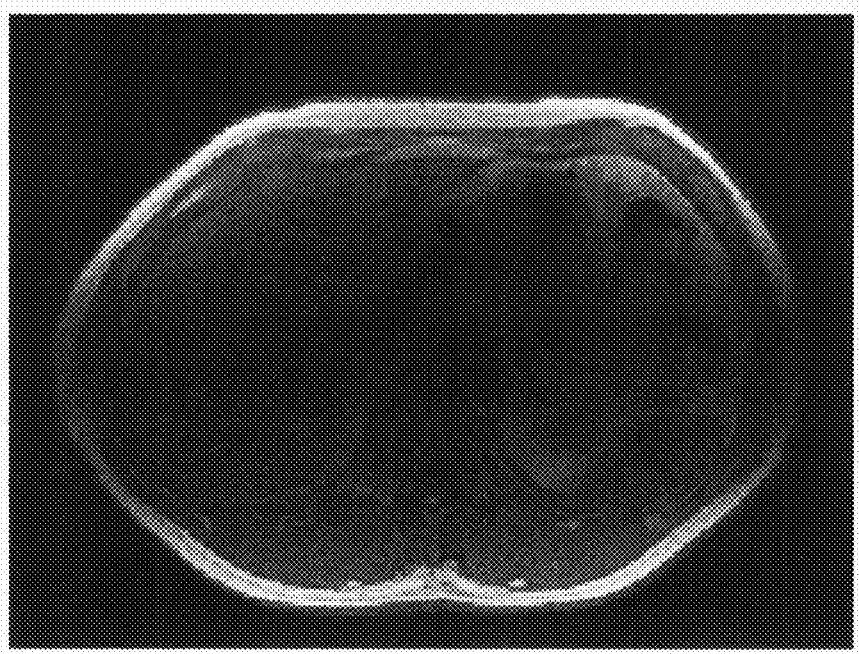
FIG. 15 shows an original image $S_{orig}$ before sensitivity correction used in the simulation of the image correction by the data correction apparatus shown in FIG. 1.
Figure 16:
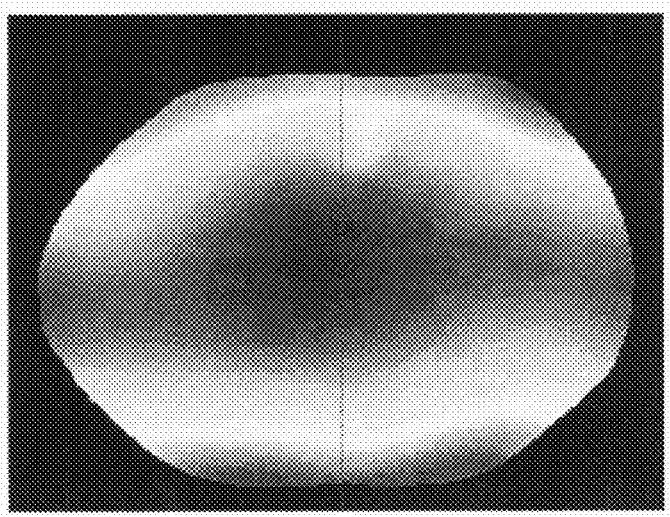
FIG. 16 shows a sensitivity distribution $I_{sens}$, which is used for sensitivity correction to the original image $S_{orig}$ shown in FIG. 15, of a coil for an abdomen and a profile thereof.
Figure 16:
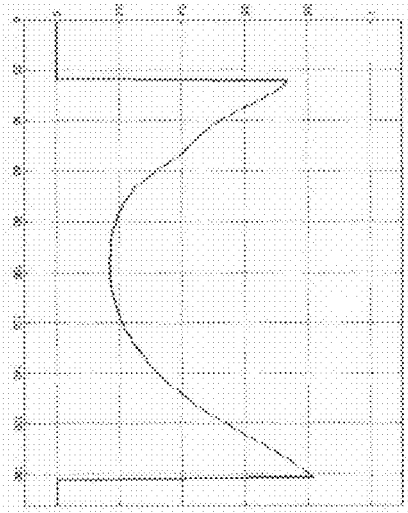
Figure 17:
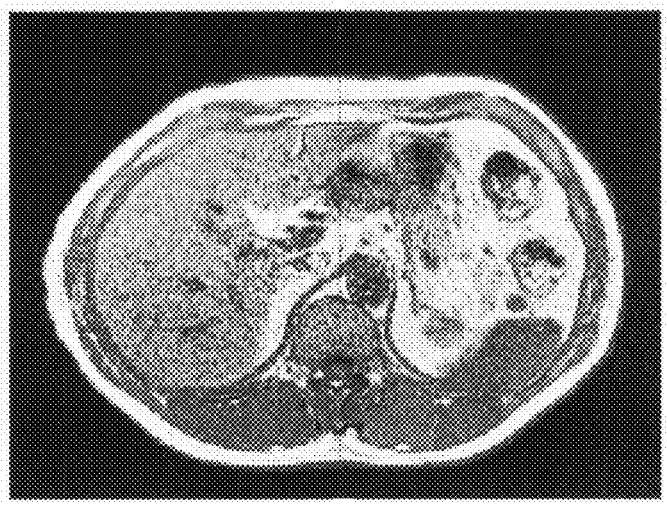
FIG. 17 shows an abdominal image $S_{orig\_scor}$ obtained by sensitivity correction to the original image $S_{orig}$ shown in FIG. 15, of a coil for an abdomen and a profile thereof.
Figure 17:
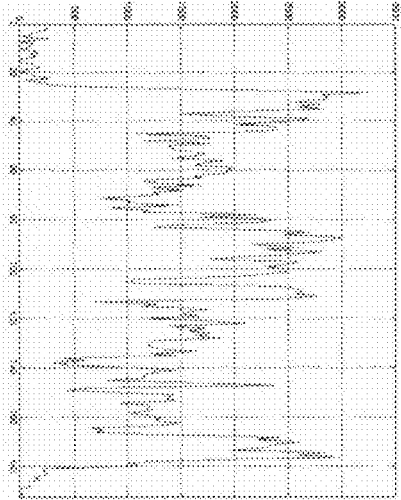
Figure 18:
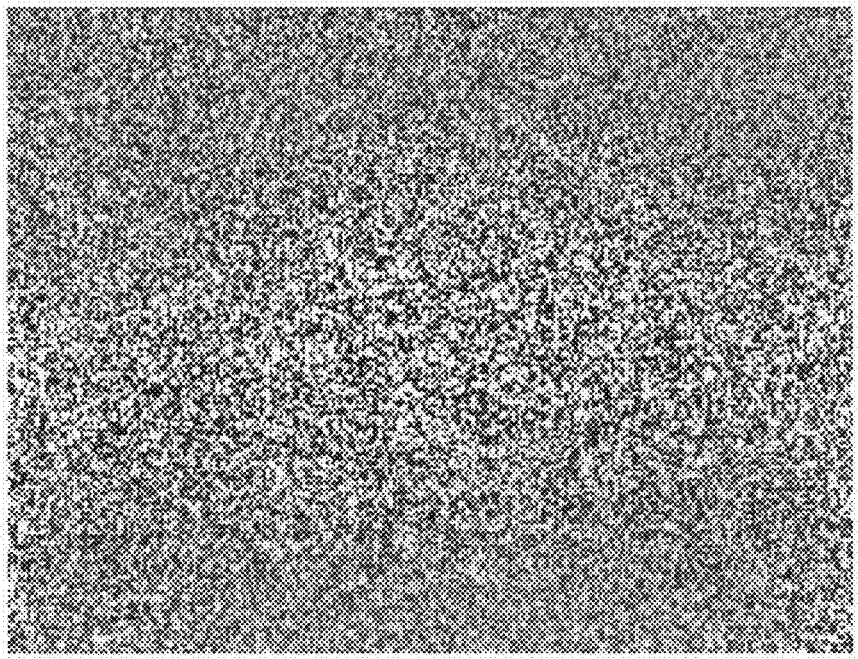
FIG. 18 shows a noise distribution noise_scor, which is used for the simulation of the image correction by the data correction apparatus shown in FIG. 1, after the sensitivity correction.

FIG. 14 shows an ideal abdominal image $S_{ideal\_scor}$ after sensitivity correction assumed on a simulation of image correction by the data correction apparatus 1 shown in FIG. 1. FIG. 15 shows an original image $S_{orig}$ before sensitivity correction used in the simulation of the image correction by the data correction apparatus 1 shown in FIG. 1. FIG. 16 shows a sensitivity distribution $I_{sens}$, which is used for sensitivity correction to the original image $S_{orig}$ shown in FIG. 15, of a coil for an abdomen and a profile thereof. FIG. 17 shows an abdominal image $S_{orig\_scor}$ obtained by sensitivity correction to the original image $S_{orig}$ shown in FIG. 15, of a coil for an abdomen and a profile thereof. FIG. 18 shows a noise distribution noise_scor, which is used for the simulation of the image correction by the data correction apparatus 1 shown in FIG. 1, after the sensitivity correction.

The original image $S_{orig}$ before the sensitivity correction shown in FIG. 15 is an image actually obtained with use of 8-ch coils for abdominal part. Also, an image obtained by performing the sensitivity correction on the original image $S_{orig}$ with the actual sensitivity distribution of the coils for abdominal part shown in FIG. 16 is the abdominal part image $S_{orig\_scor}$ shown in FIG. 17. It should be noted that in the profile of FIG. 16, the horizontal axis represents the normalized sensitivity distribution and the vertical axis represents a one-dimensional spatial position. Also, in the profile of FIG. 17, the horizontal axis represents the signal intensity of the abdominal part image $S_{orig\_scor}$ and the vertical axis represents a one-dimensional spatial position thereof.

In addition, in order that the noise distribution noise_scor shown in FIG. 18 is obtained, Gaussian noise in which a standard deviation (SD) is 1 is supplied to an image with a sufficiently high SNR through a simulation, and SNR=50 is established. That is, the noise before the sensitivity correction is set as shown in Expression (26) with use of a maximum value max ($S_{ideal}$) of ideal image data $S_{ideal}$ before the sensitivity correction, the Gaussian noise, and the SNR (=50).

$$noise=max(S_{ideal})/SNR*(Gaussian\ noise) \quad (26)$$

Then, the weighting function $W_{snr}$ is set as being normalized with use of the sensitivity distribution of each coil for abdominal part in the slice cross section so that the maximum value max=1 and the minimum value min=0 are established.

Under such conditions, as the uniform filter, the LSI filter and a structure adaptive type DSA (directional structure adaptive) filter are used to conduct the image correction simulation.

Figure 19:
FIG. 19 shows an image obtained by performing SNR correction with a uniform LSI filter to the abdominal image $S_{orig\_scor}$ after sensitivity correction shown in FIG. 17 and a profile thereof.
Figure 19:
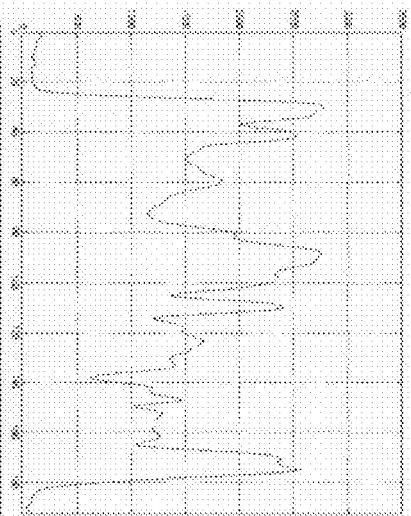
Figure 20:
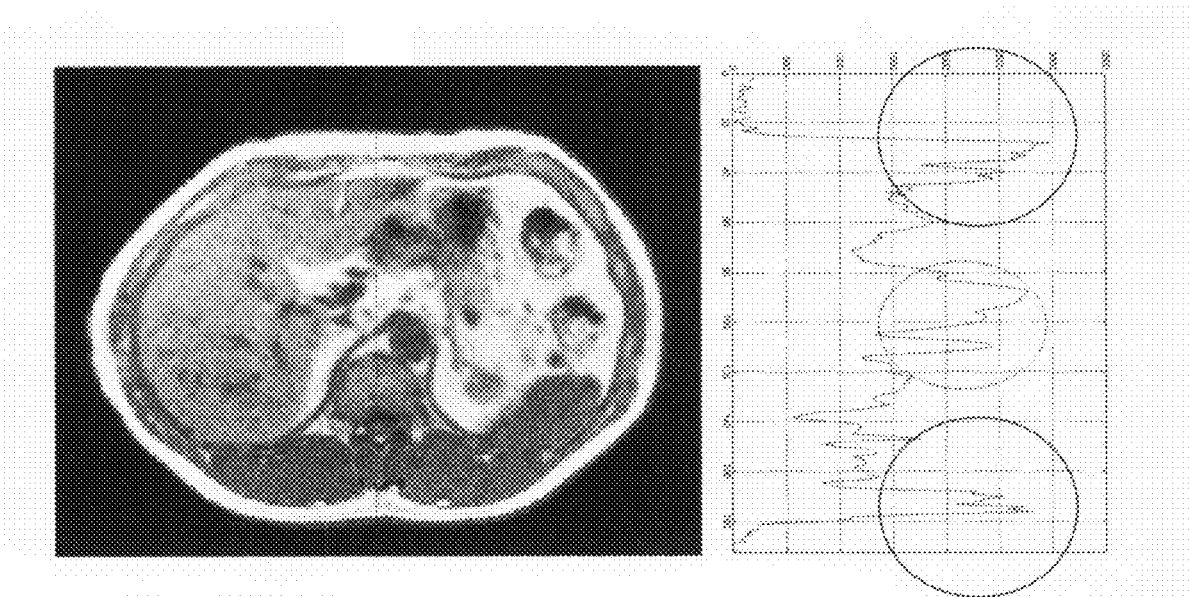
FIG. 20 shows an image obtained by performing SNR non-uniform correction accompanying weighted addition with a LSI filter to the abdominal image $S_{orig\_scor}$ after sensitivity correction shown in FIG. 17 and a profile thereof.
Figure 21:
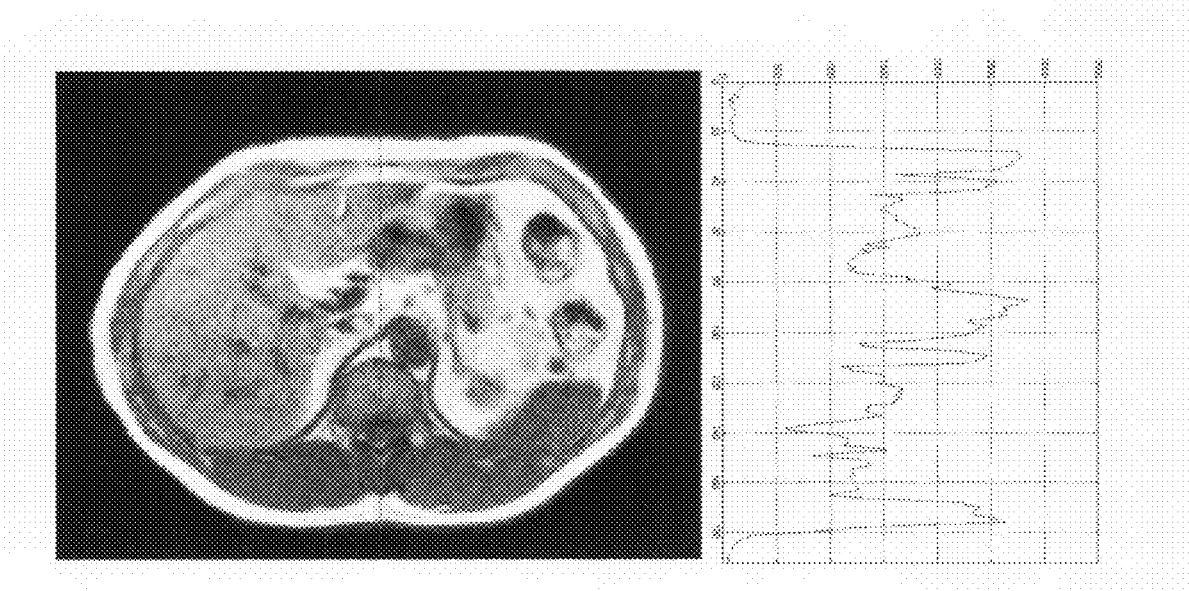
FIG. 21 shows an image obtained by performing SNR correction with a uniform structure adaptive filter to the abdominal image $S_{orig\_scor}$ after sensitivity correction shown in FIG. 17 and a profile thereof.
Figure 22:
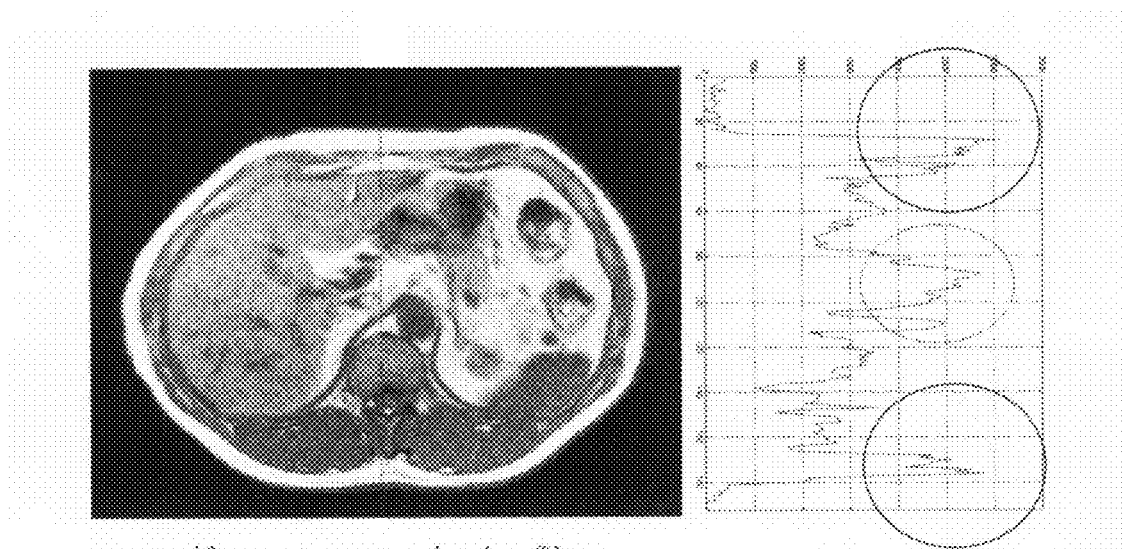
FIG. 22 shows an image obtained by performing SNR non-uniform correction accompanying weighted addition with a uniform structure adaptive filter to the abdominal image $S_{orig\_scor}$ after sensitivity correction shown in FIG. 17 and a profile thereof.

FIG. 19 shows an image obtained by performing SNR correction with a uniform LSI filter to the abdominal image $S_{orig\_scor}$ after sensitivity correction shown in FIG. 17 and a profile thereof. FIG. 20 shows an image obtained by performing SNR non-uniform correction accompanying weighted addition with a LSI filter to the abdominal image $S_{orig\_scor}$ after sensitivity correction shown in FIG. 17 and a profile thereof. FIG. 21 shows an image obtained by performing SNR correction with a uniform structure adaptive filter to the abdominal image $S_{orig\_scor}$ after sensitivity correction shown in FIG. 17 and a profile thereof. FIG. 22 shows an image obtained by performing SNR non-uniform correction accompanying weighted addition with a uniform structure adaptive filter to the abdominal image $S_{orig\_scor}$ after sensitivity correction shown in FIG. 17 and a profile thereof.

The horizontal axis in each of the profiles of FIG. 19, 20, 21, or 22 represents the signal intensity of the abdominal part image after the filter processing and the vertical axis represents a one-dimensional spatial position thereof.

As shown in FIGS. 20 and 22, through the correction of the nonuniform SNR with use of the LSI filter and the DSA filter, such an image is obtained that the smoothing is weak in the vicinity of an area surrounded by the solid line where the SNR is high and the smoothing is strong in the center area surrounded by the dotted line where the SNR is low. As a result, as compared with an image obtained while a uniform correction is conducted by using the LSI filter and the DSA filter shown in FIGS. 19 and 21, an image obtained through the correction of the nonuniform SNR with use of the LSI filter has such characteristics that the high frequency part remains more in the peripheral area and the noise is more strongly suppressed in the center area. In other words, through the correction of the nonuniform SNR, it can be confirmed that the lack of sharpness is suppressed in the peripheral area where the SNR is high and on the other hand the SNR is improved in the center area where the SNR is low.

Figure 23:
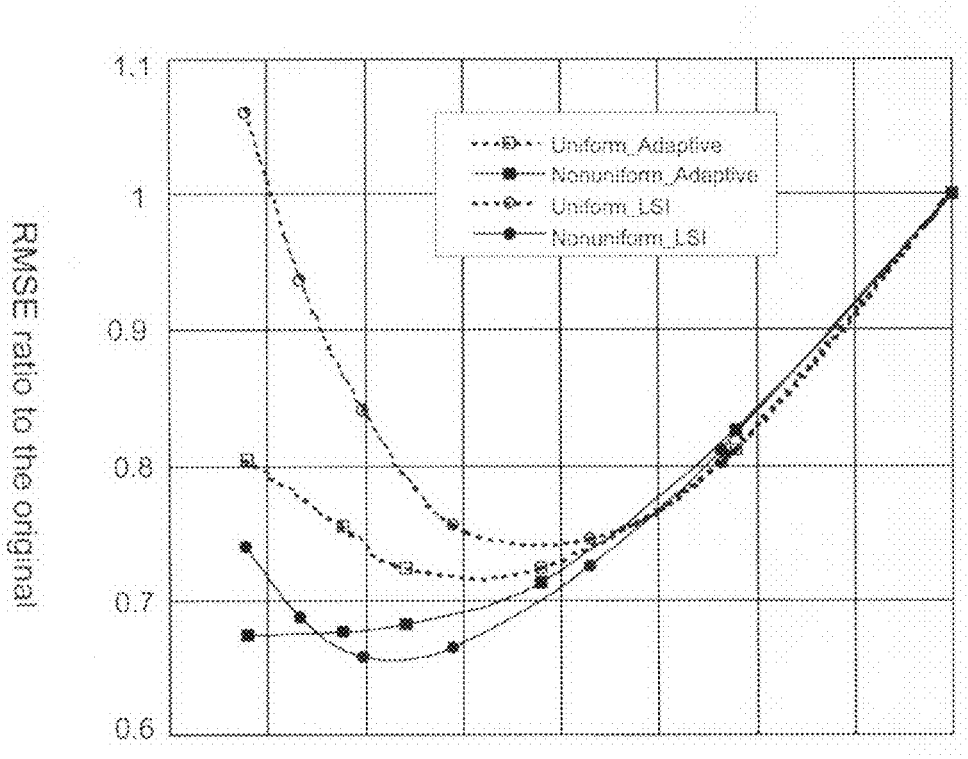
FIG. 23 is a diagram showing variations of standard deviation and RMSE of noise in case of performing filter processing with changing a smoothing intensity in the simulation of the image correction by the data correction apparatus shown in FIG. 1.

FIG. 23 is a diagram showing variations of standard deviation and RMSE of noise in case of performing filter processing with changing a smoothing intensity in the simulation of the image correction by the data correction apparatus 1 shown in FIG. 1.

In FIG. 23, the horizontal axis represents a ratio "noise SD ratio" of a standard deviation "noise SD" of the noise after the filter processing to a standard deviation "noise SDoriginal" of the original noise before the filter processing (after the sensitivity correction) and the vertical axis represents a ratio "RMSE ratio" of a root mean square error "RMSE" after the filter processing to a "RMSEoriginal" before the filter processing. Herein, the RMSE after the filter processing is calculated on the basis of the ideal image data after the sensitivity correction shown in FIG. 14.

Also in FIG. 23, the dotted line and white squire mark represent data at the time when the uniform filter processing with use of the DSA filter is performed, the solid line and filled squire mark represent data at the time when the nonuniform filter processing with use of the DSA filter is performed, the dotted line and white circle represent data at the time when the uniform filter processing with use of the LSI filter is performed, and the solid line filled and circle represent data at the time when the non-uniform filter processing with use of the LSI filter is performed.

According to FIG. 23, in the uniform filter processing with use of the LSI filter and the DSA filter, when the smoothing intensity is increased, the RMSE is gradually decreased along with the standard deviation of the noise. Once the smoothing intensity exceeds a certain level, it shows a tendency that the standard deviation of the noise is decreased and the RMSE is increased. In contrast to this, when the nonuniform filter processing with use of the LSI filter is performed, the RMSE is improved as compared with a case where the uniform filter processing with use of the LSI filter is conducted, and even when the smoothing is strong and the standard deviation of the noise is small, it can be confirmed that the RMSE is suppressed to a relatively small level.

Furthermore, in the nonuniform filter processing with use of the DSA filter, as compared with the nonuniform filter processing with use of the LSI filter, the minimum value of the RMSE is rather large, but even when the smoothing intensity is strong, it can be confirmed that the degradation in the RMSE is small. Therefore, in the nonuniform filter processing with use of the DSA filter, even with regard to an image in the center area where the SNR is low and the smoothing intensity is strong, it can be confirmed that the lack of sharpness can be made small.

In addition, the ideal image $S_{ideal\_scor}$ is unknown in the actual image data, and therefore it is impossible to obtain the RMSE. Thus, it is shown that the nonuniform filter processing with the DSA filter is superior in terms of robustness for the selection of filter intensities.

(Method for Determining a Filter Intensity)

Next, a description will be given of a determination method for the smoothing intensity in the above-mentioned uniform filter. As described above, in accordance with the SNR distribution of the data that is the correction target, it is important to optimally determine the smoothing intensity of the uniform filter. In view of the above, two methods for optimally determining the smoothing intensity will be described.

The nonuniform filtering is performed on data having the nonuniform SNR distribution, and it is ideal to minimize the RMSE to the ideal data of the signal composition distribution in the respective parts of the data. However, as the signal distribution of the ideal data is unknown, in a normal processing, it can be also said that it is impossible to minimize the RMSE. On the other hand, the signal component distribution of the data varies depending on the data. However, as shown in the result of the image correction simulation, it is found out that when the data after the sensitivity correction is subjected to the filtering with use of the LSI filter, the high frequency component is degraded at such a degree that cannot be ignored, whereas when the data after the sensitivity correction is subjected to the filtering with use of the structure adaptive filter such as the DSA filter, the degradation in the high frequency component can be minimized.

In view of the above, a description will be given of the first determination method for the smoothing intensity for determining the smoothing intensity optimal condition at which the noise SD distribution in each part of the data is set uniform when the structure adaptive filter is mainly used and the second determination method for the smoothing intensity for determining the smoothing intensity optimal condition at which the RMSE to the ideal data is to be minimized with respect to the signal composition distribution in each part of the data while it is assumed that a high general versatility filter including the LSI filter is used.

First of all, a description will be given of the first determination method for the smoothing intensity.

In general, the white noise distributes with uniform gain in the frequency axis direction in the k-space. Therefore, after the filtering with a normal LSI filter, the spatial integral value of the filter function in the k-space and the noise SD measured in the part having no signal of the real space have a proportional relation therebetween. For simplicity, a one-dimensional LSI filter in the x axis direction is considered. Thus, when the filter function of the LSI filter is set as H (kx) and the noise SD measured in the part having no signal of the real space is set as $\sigma_n$, an integral value AH of the filter function H (kx) in the k-space can be represented as Expression (27) where a is set as a proportional coefficient.

$$A_H = \int_{-K_x/2}^{K_x/2} H(k_x) dk = a\sigma_n \tag{27}$$

wherein Kx denotes a width of frequency band.

That is, the frequency bandwidth Kx is a sampling frequency band −Kx/2 to Kx/2 in each axis in the case of being expressed in the discrete system. Also, it is assumed that the Nyquist frequency that is ½ of the frequency bandwidth Kx is sufficiently larger than the maximum frequency that the target data has and the folded error can be ignored.

In Expression (27), the integral value AH of the filter function H (kx) in the k-space can be calculated if the filter function H (kx) is given. Also, the noise SD $\sigma_n$ can be measured from the noise in the part having no signal of the real space before the sensitivity correction or the noise SD in the high frequency part in the k-space.

On the other hand, an SNR ratio $SNRR_{lh}$ of the minimum SNR part of the data having the nonuniform SNR distribution before the filtering to the maximum SNR part can be represented as Expression (28) with use of the SNR distribution $I_{sens}$ that is obtained from the sensitivity distribution of the sensor (coil) when the noise SD of the minimum SNR part after the sensitivity correction is set as $\sigma_{nl}$ and the noise SD of the maximum SNR part is set as $\sigma_{nh}$.

$$\begin{aligned} SNRR_{lh} &= (1/\sigma_{nl})/(1/\sigma_{nh}) \\ &= \sigma_{nh}/\sigma_{nl} \\ &= \{\sigma_n/\max(I_{sens})\}/\{\sigma_n/\min(I_{sens})\} \\ &= \min(I_{sens})/\max(I_{sens}) \end{aligned} \tag{28}$$

That is, it is unnecessary to measure the noise SD to obtain the ratio between the minimum value and the maximum value of the SNR, and the absolute amount of noise can be obtained if the measurement is conducted before the sensitivity correction.

Figure 24:
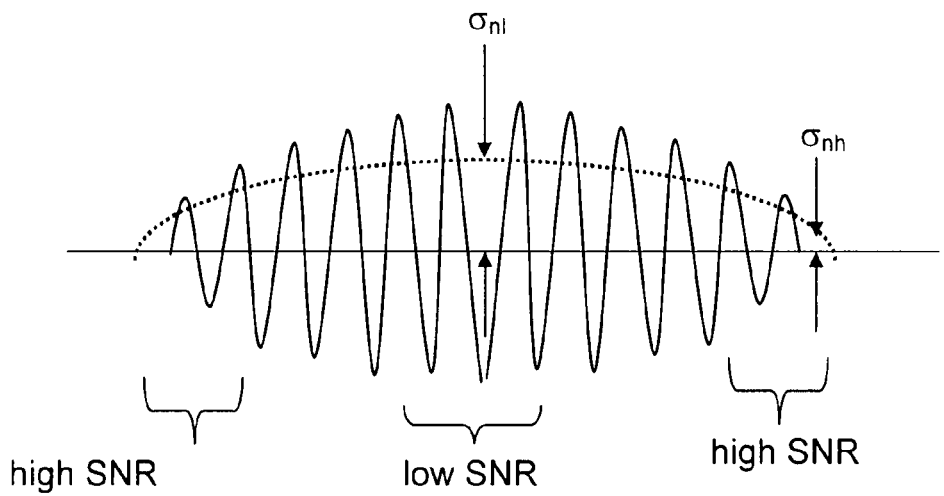
FIG. 24 is a conceptual diagram indicating non-uniform distribution and standard deviation of noise after sensitivity correction and before non-uniform filtering by the data correction apparatus.
Figure 25:
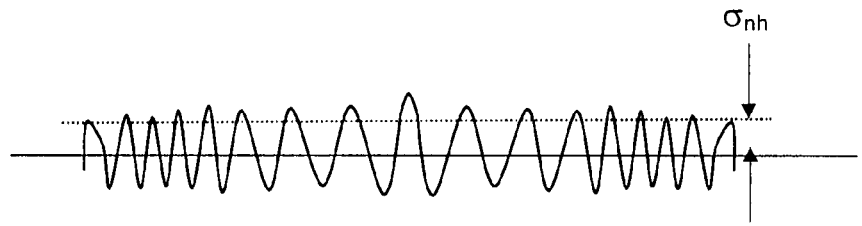
FIG. 25 is a conceptual diagram indicating distribution and standard deviation of noise obtained by uniforming non-uniform distribution of noise shown in FIG. 24 with non-uniform filtering.

FIG. 24 is a conceptual diagram indicating non-uniform distribution and standard deviation of noise after sensitivity correction and before non-uniform filtering by the data correction apparatus 1. FIG. 25 is a conceptual diagram indicating distribution and standard deviation of noise obtained by uniforming non-uniform distribution of noise shown in FIG. 24 with non-uniform filtering.

In FIGS. 24 and 25, each abscissa indicates spatial position and each ordinate indicates power and standard deviation of noise. Furthermore, in FIGS. 24 and 25, each solid line shows distribution of noise and each dotted line shows SD of noise.

As shown in FIG. 24, the noise before the nonuniform filtering is performed on the data distributes spatially nonuniformly where there are a high SNR part (high SNR) with the small noise power and the high SNR and a low SNR part (low SNR) with the large noise power and the low SNR. In addition, the noise SD $\sigma_{nh}$ in the high SNR part (high SNR) and the noise SD $\sigma_{nl}$ in the low SNR part (low SNR) can be expressed as shown in FIG. 24.

The noise SD shown in FIG. 24 changes along with the SNR through the nonuniform filtering to be set uniform as shown in FIG. 25. That is, the SD of the entire noise is reduced by the nonuniform filtering so as to be aligned with the noise SD $\sigma_{nh}$ in the high SNR part (high SNR) before the nonuniform filtering. As a result, on the whole, the noise SD after the nonuniform filtering uniformly becomes equivalent to the noise SD $\sigma_{nh}$ of the high SNR part (high SNR) before the nonuniform filtering.

Herein, it is assumed that the data after the uniform filtering with the LSI filter on the data of the minimum SNR part (low SNR) and the data after the uniform filtering on the data of the maximum SNR part (high SNR) are synthesized to each other to respectively have weights of 1 and 0, whereby the entire data is subjected to the nonuniform filtering as a result. Then, the SNR of the data (in the vicinity of the center of FIG. 25) after the nonuniform filtering on the data of the minimum SNR part (low SNR) is equivalent to the SNR after the uniform filtering, and the SNR of the data (in the vicinity of the end part of FIG. 25) after the nonuniform filtering on the data of the maximum SNR part (high SNR) is equivalent to the SNR before the uniform filtering. In other words, the SNR of the minimum SNR part (low SNR) before the nonuniform filtering is equivalent to the SNR before the uniform filtering, and the SNR of the maximum SNR part (high SNR) before the nonuniform filtering is equivalent to the ideal SNR after the uniform filtering.

Herein, when a ratio between the SNRs before and after the uniform filtering with the LSI filter is set as $SNRR_{fil.lh}$, the SNR ratio $SNRR_{fil.lh}$ can be represented as Expression (29) using integral values $A_{Hl}$ and $A_{Hh}$ of the filter functions which are applied to the minimum SNR part (low SNR) and the maximum SNR part (high SNR) respectively.

$$SNRR_{fil.lh}=A_{Hl}/A_{Hh} \tag{29}$$

Therefore, an attempt in order to obtain the optimal condition where the smoothing intensity optimal condition is set as "a condition with which the noise SD in each part of the data having the nonuniform SNR becomes the noise SD in the maximum SNR part" as shown in FIG. 25 boils down to the question of determining the integral value $A_{Hl}$ of the filter function Hl (kx) to be applied to the minimum SNR part (low SNR) so that the right-side member of Expression (28) and the right-side member of Expression (29) are equal to each other or in proportion. In other words, the integral value of the filter function should be controlled such that the SNR distribution of the data that is the filtering target is set as the inverse number of the noise SD in the part having no signal of the real space data after the sensitivity correction, and the ratio between the minimum value and the maximum value of the SNR distribution becomes in proportion (also including the identical case and the case of a proportional coefficient times) to the ratio between the integral value of the filter function to a part where the SNR becomes minimum and the integral value of the filter function to a part where the SNR becomes maximum.

Therefore, on the basis of Expression (28) and Expression (29), the integral value $A_{Hl}$ of the filter function Hl (kx) can be determined as shown in Expression (30).

$$A_{Hl}=A_{Hh}*SNRR_{lh}=A_{Hh}*\min(I_{sens})/\max(I_{sens}) \tag{30}$$

Herein, if it is assumed that the noise SD in the maximum SNR part (high SNR) is not changed by the LSI filter, the LSI filter to be applied to the maximum SNR part (high SNR) can be considered as being equivalent to the filter having the gain of 1, and therefore the integral value $A_{Hh}$ of the filter function of the LSI filter to be applied to the maximum SNR part (high SNR) can be defined as shown in Expression (31).

$$A_{Hh}=\int_0^{K_x} 1 \, dk_x = K_x \tag{31}$$

Therefore, when the result of Expression (31) is assigned to Expression (30), Expression (32) is obtained.

$$A_{Hl}=SNRR_{lh}*K_x \tag{32}$$

According to Expression (32), if the ratio $SNRR_{lh}$ between the noise SD in the maximum SNR part (high SNR) and the noise SD in the minimum SNR part (low SNR) and the sampling frequency band Kx are found out, it is understood that the integral value $A_{Hl}$ of the filter function Hl (kx) that should be applied to the minimum SNR part (low SNR) can be determined.

Incidentally, in a case where the filter function Hi (kx) for providing the integral value $A_{Hl}$ shown in Expression (32) is determined, the constraint condition is only the integral value, and thus the flexibility for designing the filter function Hl (kx) is large. It should be noted that generally, the filter function Hl (kx) is preferable to be a function in which the gain is decreased to the higher frequency component. In view of the above, for example, the filter function Hl (kx) is set as a Hanning function shown in Expression (33).

$$H(k_x)=0.5\{1+\cos(b_x*k_x/K_x)\}:|k_x|<K_x/b_x; =0: \text{otherwise} \tag{33}$$

It should be noted that, bx denotes a parameter for determining the cutoff frequency of the LSI filter and when bx=2, the cutoff frequency becomes equal to the sampling maximum/minimum frequency$\pm K_x/2$.

Figure 26:
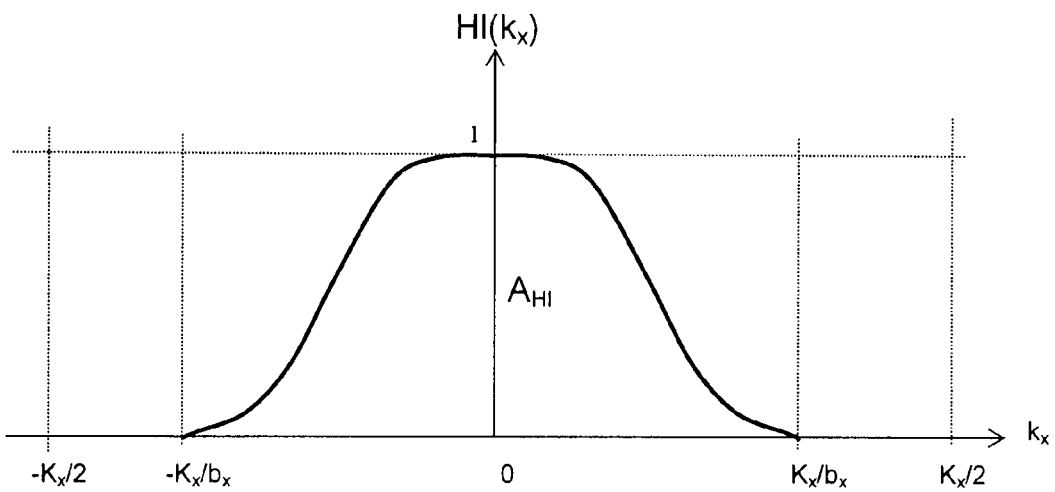
FIG. 26 is a diagram showing an example in case that a filter function of a uniform filter in the data correction apparatus is a Hanning function.

FIG. 26 is a diagram showing an example in case that a filter function of a uniform filter in the data correction apparatus is a Hanning function.

In FIG. 26, the abscissa indicates a frequency axis kx and the ordinate indicates a filter function Hl(kx). As shown in FIG. 26, the area of part surrounded by the filter function Hl (kx) and the frequency axis kx is the integral value $A_{Hl}$ of the filter function Hl (kx) to be determined under Expression (32). Also, while the parameter bx is adjusted, the cutoff frequency of the LSI filter can be arbitrarily set in the range of the sampling maximum/minimum frequency$\pm K_x/2$.

When the filter function Hl (kx) is defined as shown in Expression (33), the integral value $A_{Hl}$ of the filter function Hl (kx) is represented as Expression (34).

$$A_{Hl} = \int_{-K_x/b_x}^{K_x/b_x} 0.5\{1 + \cos(b*k_x/K_x)\} dk_x \tag{34}$$
$$= 2\int_0^{K_x/b_x} 0.5\{1 + \cos(b_x*k_x/K_x)\} dk_x$$
$$= K_x/b_x$$

Therefore, Expression (35) is derived from Expression (32) and Expression (34).

$$SNRR_{lh}=A_{lh}/A_l=K_x/b_xK_x=1/b_x \tag{35}$$

Then, when Expression (35) is expressed with regard to the parameter bx, Expression (36) is obtained.

$$b_x=1/SNRR_{lh}=\sigma_{nl}/\sigma_{nh} \tag{36}$$

According to Expression (36), it is understood that the parameter bx may be determined with use of the ratio $SNRR_{lh}$ between the noise SD in the maximum SNR part (high SNR) and the noise SD in the minimum SNR part (low SNR) given by Expression (28).

When the filter function Hl (kx) of the LSI filter is determined through such a method and the nonuniform SNR correction is conducted by the above-mentioned weighted addition, it is possible to obtain the optimal data while the noise SD distribution is set uniform.

It should be noted that when the noise distributes in the normal three dimensions the relation between the integral value AH of the filter function H (Kx, Ky, Kz) in the k-space (Kx, Ky, Kz) and the noise SD $\sigma_n$ is as shown in Expression (37) when the proportional coefficient is set as a.

$$A_H = \int_0^{K_z} \int_0^{K_y} \int_0^{K_x} H(k_x, k_y, k_z) dk_x dk_y dk_z = a\sigma_n \tag{37}$$

Herein, if the filter function H (Kx, Ky, Kz) is a function expressed as a direct product type as shown in Expression (38-1), the integral values $A_{Hl}$ and $A_{Hh}$ of the filter functions H (Kx, Ky, Kz) to be respectively applied to the minimum SNR part (low SNR) and the maximum SNR part (high SNR) are represented as Expression (38-2) and Expression (38-3) respectively.

$$H(k_x, k_y, k_z) = H(k_x)H(k_y)H(k_z) \quad (38\text{-}1)$$

$$A_{Hh} = K_x K_y K_z \quad (38\text{-}2)$$

$$A_{Hl} = SNRR_{lh} * K_x K_y K_z \quad (38\text{-}3)$$

It should be noted that the LSI filter to be applied to the maximum SNR part (high SNR) is assumed to be a filter having the gain of 1.

According to Expression (38-3), it is understood that as in the case where the noise distributes one-dimensionally, the integral values $A_{Hl}$ and $A_{Hh}$ of the filter functions H (Kx, Ky, Kz) can be obtained on the basis of the ratio $SNRR_{lh}$ between the noise SD in the maximum SNR part (high SNR) and the noise SD in the minimum SNR part (low SNR) given by Expression (28).

In particular, when the filter function H (Kx, Ky, Kz) is defined with use of the Hanning function having parameters bx, by, and bz, Expression (39) is derived.

$$\begin{aligned} SNRR_{lh} &= A_h/A_l \\ &= (K_x/b_x K_x)(K_y/b_y K_y)(K_z/b_z K_z) \\ &= 1/(b_x b_y b_z) \end{aligned} \quad (39)$$

Therefore, a product bxbybz of the parameters bx, by, and bz of the Hanning function can be obtained according to Expression (39). Herein, if the three-dimensional filter function H (Kx, Ky, Kz) defined by the Hanning function is a function of an origin symmetry type, bx=by=bz=b can be established. Accordingly, Expression (39) is expressed as Expression (40).

$$SNRR_{lh} = 1/b^3 \quad (40)$$

Therefore, according to Expression (40), the parameter b of the filter function H (Kx, Ky, Kz) can be uniquely determined on the basis of the ratio $SNRR_{lh}$ between the noise SD in the maximum SNR part (high SNR) and the noise SD in the minimum SNR part (low SNR).

The optimal determination method for the smoothing intensity of the uniform filter in the case where the optimal condition is that the noise SD is set uniform has been described above. Furthermore, in order to achieve the matching with respect to the visual optimality of the image data or make an association with the absolute SNR, a coefficient may be introduced. This coefficient may be a constant or a variable.

For example, the mean SNR is set as SNRm and the SNRm is represented as Expression (41).

$$SNRm = S(DC)/\sigma n \quad (41)$$

It should be noted that S (DC) denotes the absolute value mean of the signals in the vicinity of DC in the k-space. That is, the SNRm is set as a ratio between an absolute value mean S (DC) of signals in the vicinity of DC in the k-space and the noise SD $\sigma_n$.

Then, a coefficient C (SNRm) using the SNRm that is the absolute SNR as a parameter is introduced and the coefficient C (SNRm) is set as such a function of the SNRm that smoothing intensity becomes larger as the SNRm is smaller. Furthermore, Expression (32) is transformed into Expression (42) with use of the coefficient C (SNRm) and the condition for the integral value $A_{Hl}$ of the filter function can be corrected.

$$A_{Hl} = C(SNR_m) * SNRR_{lh} * K_x \quad (42)$$

In addition, when the structure adaptive filter is used for the nonuniform SNR correction, the noise SD after the filtering basically depends also on the signal distribution of the data in the real space. It should be noted that if the noise SD is defined with the SD in the flat part or the part having no signal of the signal in the real space, as in the case of using the LSI filter, the integral value of the filter function of the structure adaptive filter can be determined. In the filtering with the LSI filter, the smoothing is stronger in the smaller SNR part and the spatial resolution is deteriorated, but in the filtering with the structure adaptive filter, uniformity of the noise distribution can be achieved while the spatial resolution is maintained, whereby it is possible to perform the correction that is even closer to the ideal.

In other words, the above-mentioned first determination method for the smoothing intensity is for determining the filter function by using the noise of the denominator of the SNR that is a direct current component.

(Application to Wiener Filter)

Next, a description will be given of the second determination method for the smoothing intensity.

The second determination method for the smoothing intensity is for determining the smoothing intensity so that the RMSE of the data is minimized in a case where a high general versatility filter such as the Wiener Filter as described above is used to perform the filtering.

A filter function Hw of the Wiener Filter (hereinafter, denoted as WF) can be ideally represented as a function with regard to a filtering space as shown in Expression (43) when the power of signal is set as Ps and the power of noise is set as Pn.

$$Hw = Ps/(Ps + Pn) \quad (43)$$

In general, the power Ps of signal is a function for a space to be applied with the WF, whereas the power Pn of noise is constant. The general space to be applied with the WF is defined by a Fourier space, and the WF defined by the Fourier space is denoted by FT-WF. It should be noted that a target to be applied with the WF can be the FREBAS space as well as any WF space divided into multiple resolutions, and the WF defined by the FREBAS space is denoted by FR-WF.

In general, in the correction on the data having the nonuniform SNR, the WF is not used for the filtering after the sensitivity correction where the noise has the spatial distribution. However, when a WF processing, which is optimized by using the power of noise in/a part where the SNR becomes maximum and the power of noise in a part where the SNR becomes minimum after the sensitivity correction, is performed and the weighted addition is performed on the data after the WF processing, it is considerable that the spatially optimal SNR correction can be realized. In view of the above, the WF is applied to the data after the sensitivity correction.

In a case where the SNR is large to some extent, the filter function Hw of the WF can be determined as an ideal type as shown in Expression (43). In this case, as the signal distribution of the ideal data is unknown, the power Ps of signal can be obtained from the data that is the filtering target. Also, in a case where the SNR is small to some extent, the filter function Hw of the WF may be set as a threshold type as shown in Expression (44) in which a threshold or lower value is regarded as zero.

$$Hw = \max[Ps - Pn, 0]/Ps \quad (44)$$

Furthermore, at the time of the determination of the above-mentioned filter function Hw, the power Ps of signal can also be obtained on the basis of a correlation between adjacent voxels. Also, the power Pn of noise may be corrected as shown in Expression (45) with use of a correction coefficient Ca.

$$Pn = Ca*Pn \qquad (45)$$

In other words, according to the above-mentioned second determination method for the smoothing intensity, the power Ps of signal in each part of the data is used as an approximate solution of the signal distribution of the ideal data when the filtering is performed through the WF, and the RMSE of the data with respect to the ideal data is minimized.

Then, with the adoption of the above-mentioned first or second determination method for the smoothing intensity, it is possible to optimize the smoothing intensity of the filter. This optimizing function for the smoothing intensity can be provided to the filter unit 4. Here, a description will be given of a processing flow for the filtering associated with the optimization in the smoothing intensity. For example, a description will be given of a case in which the filtering associated with the optimization in the smoothing intensity is conducted in the filter unit 4 of the data correction apparatus 1 shown in FIG. 1.

Figure 27:
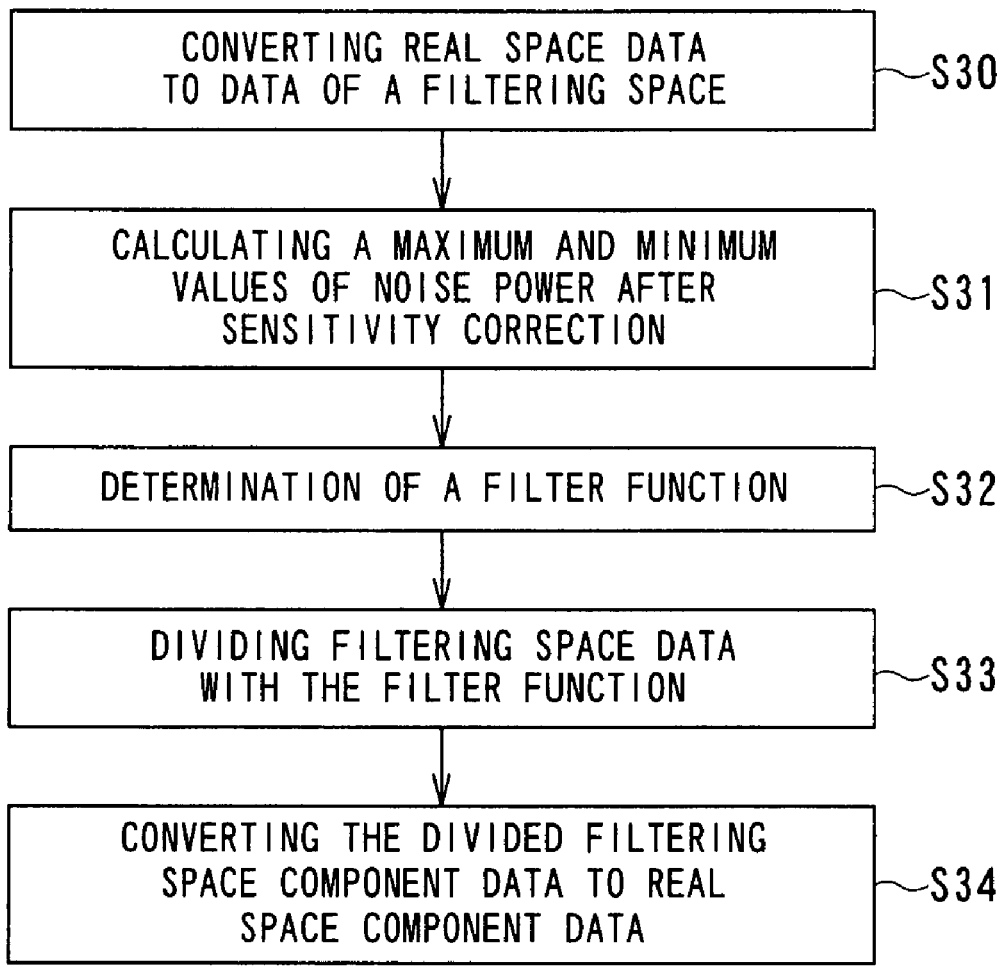
FIG. 27 is a flowchart showing a processing flow in case of filtering with optimization of smoothing intensity of the uniform filter in the filter unit of the data correction apparatus shown in FIG. 1.

FIG. 27 is a flowchart showing a processing flow in case of filtering with optimization of smoothing intensity of the uniform filter in the filter unit 4 of the data correction apparatus 1 shown in FIG. 1. The symbols including S with a number in FIG. 27 indicate each step of the flowchart.

First of all, in Step S30, the data in the real space that is the filtering target is converted into data in the filtering space. When the filtering is conducted on the image data with the FT-WF, the image data $S_{scor}$ (x, y, z) in the real space after the sensitivity correction is subjected to the FT to convert the image data $S_{scor}$ (x, y, z) into the data $S_{scor}$ (kx, ky, kz) in the k-space (kx, ky, kz) as shown in Expression (46-1). At the same time, for a processing to be described later, the image data $S_{orig}$ (x, y, z) in the real space before the sensitivity correction is subjected to the FT to be converted into the data $S_{orig}$ (kx, ky, kz) in the k-space (kx, ky, kz) as shown in Expression (46-2).

$$S_{scor}(kx,ky,kz)=FT[S_{scor}(x,y,z)] \qquad (46\text{-}1)$$

$$S_{orig}(kx,ky,kz)=FT[S_{orig}(x,y,z)] \qquad (46\text{-}2)$$

It should be noted that when the filtering is conducted on the image data with the FR-WF, the FREBAS transfer is used instead of the FT for the conversion into the data on the FREBAS space. Hereinafter, a description will be given of a case where the filtering is conducted on the image data with the FT-WF.

Next, in Step S31, the minimum value Pnl and the maximum value Pnh of the power of noise after the sensitivity correction are obtained from the power $Pn_{orig}$ of noise before the sensitivity correction and the sensitivity distribution $I_{sens}$ (x, y, z) of the sensor. That is, the power $Pn_{orig}$ of noise before the sensitivity correction is obtained from the high frequency part in the k-space data $S_{orig}$ (kx, ky, kz) before the sensitivity correction. Then, on the basis of Expression (47-1) and Expression (47-2), the maximum value Pnh and the minimum value Pnl of the power of noise after the sensitivity correction are obtained.

$$Pnl=Pn\text{orig}/\min[I_{sens}(x,y,z)] \qquad (47\text{-}1)$$

$$Pnh=Pn\text{orig}/\max[I_{sens}(x,y,z)] \qquad (47\text{-}2)$$

Next, in Step S32, on the basis of the minimum value Pnl and the maximum value Pnh of the power of noise after the sensitivity correction, the filter function Hwh (kx, ky, kz) of the WF to a part where the SNR becomes maximum and the filter function Hwl (kx, ky, kz) of the WF to a part where the SNR becomes minimum are obtained with Expression (43) or Expression (44).

Next, in Step S33, as shown in Expression (48-1) and Expression (48-2), the WF defined by the filter function Hwl (kx, ky, kz) and Hwh (kx, ky, kz) of two types of the smoothing intensities are applied to the k-space data $S_{scor}$ (kx, ky, kz) after the sensitivity correction, thereby dividing the k-space data $S_{scor}$ (kx, ky, kz) into two pieces of k-space component data, data $S_{scor.fil.l}$ (kx, ky, kz) and data $S_{scor.fil.h}$ (kx, ky, kz).

$$S_{scor.fil.l}(kx, ky, kz) = Hwl(kx, ky, kz) * S_{scor}(kx, ky, kz) \qquad (48\text{-}1)$$

$$S_{scor.fil.h}(kx, ky, kz) = Hwh(kx, ky, kz) * S_{scor}(kx, ky, kz) \qquad (48\text{-}2)$$

Next, in Step S34, as shown in Expression (49-1) and Expression (49-2), the k-space component data $S_{scor.fil.l}$ (kx, ky, kz) and the k-space component data $S_{scor.fil.h}$ (kx, ky, kz) in the filtering space are respectively converted through IFT (inverse Fourier transform) into real space component data $S_{scor.fil.l}$ (x, y, z) and $S_{scor.fil.h}$ (x, y, z).

$$S_{scor.fil.l}(x,y,z)=IFT[S_{scor.fil.l}(kx,ky,kz)] \qquad (49\text{-}1)$$

$$S_{scor.fil.h}(x,y,z)=IFT[S_{scor.fil.h}(kx,ky,kz)] \qquad (49\text{-}2)$$

Then, the thus obtained real space component data $S_{scor.fil.l}$ (x, y, z) and the real space component data $S_{scor.fil.h}$ (x, y, z) are supplied to the weighted addition unit 5 as the output data from the filter unit 4. Then, as described above, the weighting function $W_{snr}$ (x, y, z) representing the distribution of the SNR obtained in the SNR distribution acquisition unit 3 is used to perform the weighted addition on the real space component data $S_{scor.fil.l}$ (x, y, z) and the real space component data $S_{scor.fil.h}$ (x, y, z), thereby generating the image data in which the nonuniform SNR distribution is corrected.

With such a processing in the filter unit 4, the non-uniform filtering associated with the optimization in the smoothing intensity can be conducted under the optimization condition where the filtering is performed by using the WF so that the RMSE is minimized while dealing with data having the non-uniform SNR distribution. It should be noted that similarly to the flow shown in FIG. 2, when the SNR after the non-uniform filtering is set as the maximum SNR before the non-uniform filtering, the WF defined by the filter function Hwh (kx, ky, kz) is not applied to the k-space data $S_{scor}$ (kx, ky, kz) and only the WF defined by the filter function Hwl (kx, ky, kz) may be applied to the k-space data $S_{scor}$ (kx, ky, kz). In this case, instead of outputting the real space component data $S_{scor.fil.h}$ (x, y, z) from the filter unit 4 to the weighted addition unit 5, the image data $S_{scor}$ (x, y, z) after the sensitivity correction is supplied as a target of the weighted addition from the sensitivity correction unit 2 to the weighted addition unit 5.

Also, as described above, in the case of the filtering with use of the FT-WF, the degradation in the spatial resolution may occur to some extent. On the other hand, if the FR-WF is used to perform the filtering, it is possible to suppress the degradation in the spatial resolution to minimum.

(Example of Application to an X-ray CT Apparatus)

Each of the data correction apparatuses 1, 1A, 1B and 1C may be built in an X-ray CT apparatus. Therefore, an example of building the data correction apparatuses 1 shown in FIG. 1 in an X-ray CT apparatus to perform sensitivity correction to projection data or X-ray CT image data acquired by a X-ray detector serving as a sensor will be described.

Figure 28:
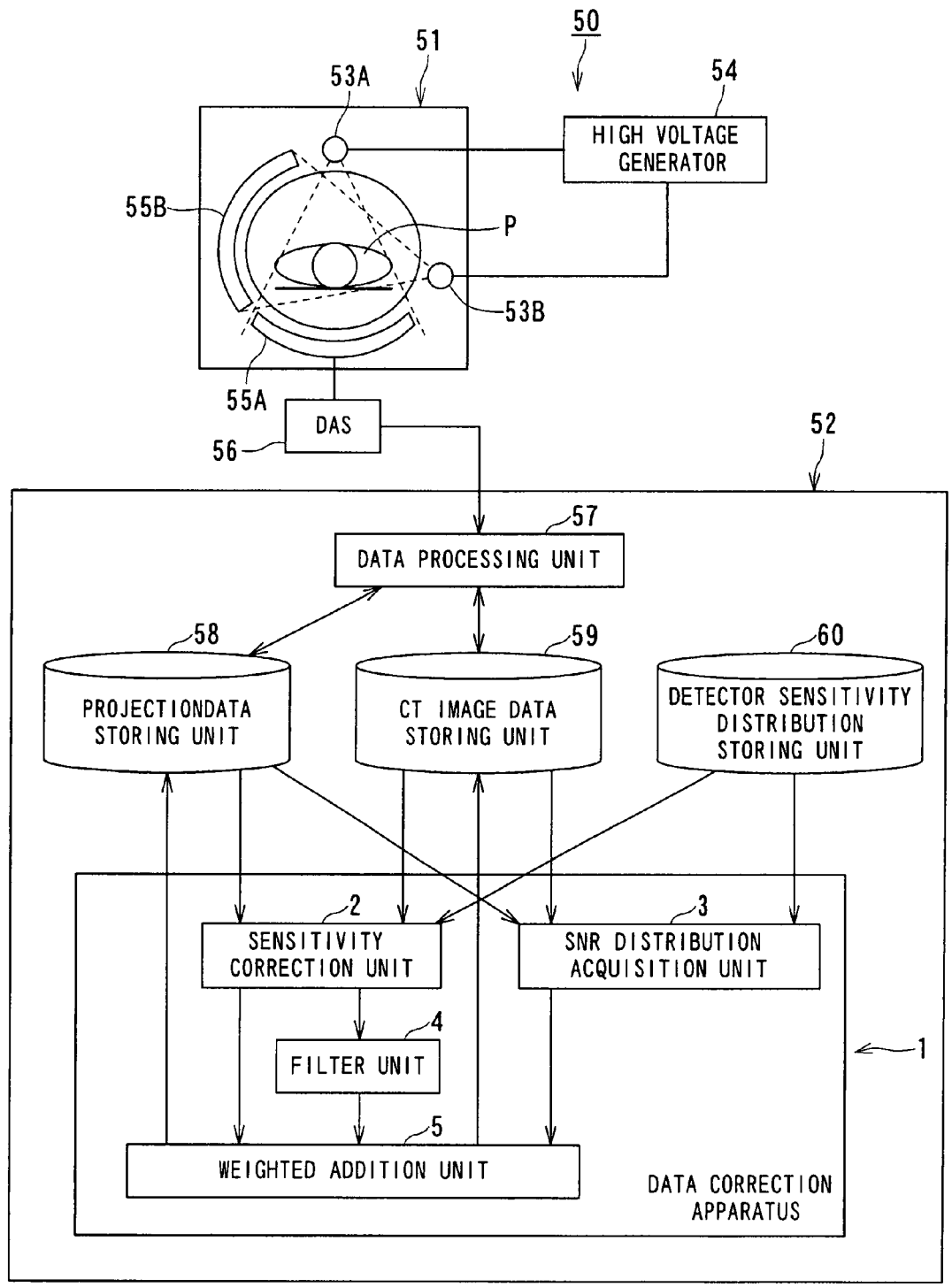
FIG. 28 is a structure diagram showing an X-ray CT apparatus according to an embodiment of the present invention.

FIG. 28 is a structure diagram showing an X-ray CT apparatus according to an embodiment of the present invention.

An X-ray CT apparatus 50 shown in FIG. 28 includes a gantry part 51 and a computer part 52. The gantry part 51 includes X-ray tubes 53, a high voltage generator 54, X-ray detectors 55 and a DAS (data acquisition system) 56. FIG. 28 shows a multitubular CT apparatus provided with the two X-ray tubes 53A and 53B and the X-ray detectors 55A and 55B. It should be noted that a single tubular CT apparatus provided with the single X-ray tube 53 and the X-ray detector 55 may also be used.

The X-ray tubes 53A and 53B and the X-ray detectors 55A and 55B are provided on a rotating ring not shown in the drawing at positions mutually opposing with the object P sandwiched.

The high voltage generator 54 is configured to supply tube currents and tube voltages to the X-ray tubes 53A and 53B respectively. The X-ray detectors 55A and 55B are configured to detect the X-rays which are exposed from the X-ray tubes 53A and 53B respectively and transmitted through the object P. Furthermore, X-ray detection signals detected by the X-ray detectors 55A and 55B respectively are supplied to the DAS 56 for digitalization to be then supplied to the computer part 52.

The computer part 52 with programs functions as a data processing unit 57, a projection data storing unit 58, a CT image data storing unit 59 and a detector sensitivity distribution storing unit 60. Furthermore, the data correction apparatus 1 shown in FIG. 1 is built in the computer part 52.

The data processing unit 57 has a function of generating projection data and X-ray. CT image data by executing various data processing on the X-ray detection signals from the DAS 56. The projection data and the X-ray CT image data produced by the data processing unit 57 are stored in the projection data storing unit 58 and the CT image data storing unit 59 respectively.

Furthermore, the detector sensitivity distribution storing unit 60 stores spatial sensitivity distribution information of the respective X-ray detectors 55A and 55B.

Then, the sensitivity correction unit 2 of the data correction apparatus 1 is configured to perform the sensitivity correction on projection data acquired from the projection data storing unit 58 or the X-ray CT image data acquired from the CT image data storing unit 59 with use of respective spatial sensitivity distribution information of the X-ray detectors 55A and 55B acquired from the detector sensitivity distribution storing unit 60.

Furthermore, the SNR distribution acquisition unit 3 is configured to estimate the distribution of the SNR generated along with the sensitivity correction on the projection data or the X-ray CT image data to with use of the sensitivity distribution information acquired from the detector sensitivity distribution storing unit 60 and the projection data obtained from the projection data storing unit 58 or X-ray CT image data obtained from the CT image data storing unit 59.

The spatial SNR distribution of the projection data can be obtained from intensities of X-ray detection signals outputted from the respective X-ray detectors 55A and 55B every channel. The spatial SNR distribution of the X-ray CT image data can be obtained from a reconstructed CT image produced at a rough matrix.

Figure 29:
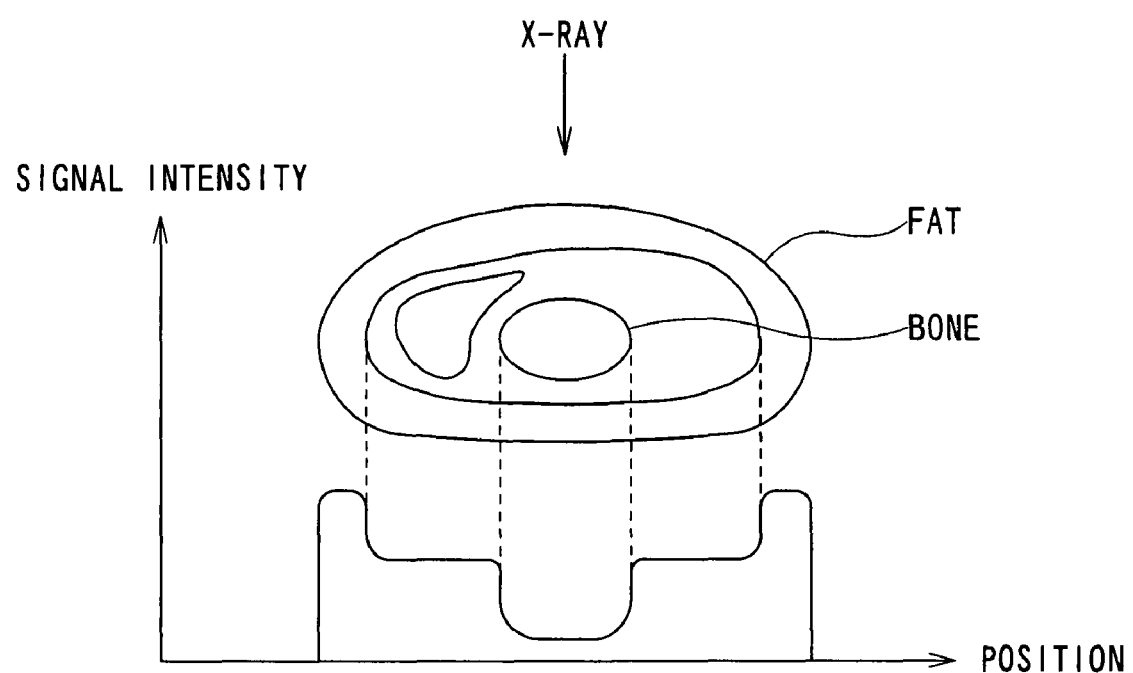
FIG. 29 is a diagram indicating relation between position in the imaging area of the X-ray CT apparatus shown in FIG. 28 and intensity of the X-ray detection signal output from each of the X-ray detectors.

FIG. 29 is a diagram indicating relation between position in the imaging area of the X-ray CT apparatus 50 shown in FIG. 28 and intensity of the X-ray detection signal output from each of the X-ray detectors 55A and 55B.

In FIG. 29, the abscissa indicates position on the imaging area and the ordinate indicates intensity of the X-ray detection signal.

When the SNR distribution of the projection data is obtained for example, a dose of an X-ray corresponding to a part of a structure, such as a bone, showing a large X-ray absorption coefficient in the projection direction as shown in FIG. 29 is reduced. Therefore, intensity distributions of the X-ray detection signals outputted from the X-ray detectors 55A and 55B are obtained with regard to all projection data. Thus, the intensity distributions of the X-ray detection signals can be used as the SNR distributions.

Furthermore, an SNR distribution (SNR) of the X-ray CT image data is equivalent to an inverse number of a CT value (CT#) of a CT image reconstructed roughly as shown by expression (50)

$$1/CT\# \propto SNR \tag{50}$$

In the X-ray CT apparatus 50, with the data correction apparatus 1, the spatially nonuniform sensitivity distribution inherent in each of the X-ray detectors 55A and 55B can be corrected while the spatial uniformity of the SNR distribution is maintained. In addition, in the X-ray CT apparatus 50, with the data correction apparatus 1, the sensitivity variation between the X-ray detectors 55A and 55B can also be corrected.

In other words, when data collected in not only the multitubular X-ray CT apparatus 50 but also a medical apparatus having a plurality of sensors is set as each correction target of the data correction apparatus 1, 1A, 1B, or 1C, it is possible to correct the respective spatial sensitivity variation of the sensors as well as a sensitivity variation between the sensors.

What is claimed is:

1. A data correction apparatus comprising:
a sensitivity correction unit configured to produce first processed data by performing sensitivity correction to first objective data obtained based on correction objective data using non-uniform sensitivity distribution of a sensor for acquiring the correction objective data; and
an SNR distribution correcting unit configured to produce pieces of component data each subjected to corresponding weighting depending on an SNR distribution and corresponding filtering having a mutually different intensity using second objective data obtained based on the correction objective data to produce second processed data by compounding the pieces of the component data,
wherein said SNR distribution correcting unit is configured to obtain a maximum power and a minimum power of noise on the first processed data after the sensitivity correction using the non-uniform sensitivity distribution, perform the corresponding filtering having the mutually different intensity to the first processed data using each of a filter function for a minimum SNR of which an intensity is determined to optimize an SNR in accordance with the maximum power and a filter function for a maximum SNR of which an intensity is determined to optimize the SNR in accordance with the minimum power and perform weighted addition of two pieces of fourth intermediate component data each produced by the corresponding filtering having the mutually different intensity.

2. A data correction apparatus comprising:
a sensitivity correction unit configured to produce first processed data by performing sensitivity correction to first objective data obtained based on correction objective data using non-uniform sensitivity distribution of a sensor for acquiring the correction objective data; and an SNR distribution correcting unit configured to produce pieces of component data each subjected to corresponding weighting depending on an SNR distribution and corresponding filtering having a mutually different intensity using second objective data obtained based on the correction objective data to produce second processed data by compounding the pieces of the component data, wherein said SNR distribution correcting unit includes a filter intensity determining unit configured to determine a filter function of a filter used for the corresponding filtering having the mutually different intensity in accordance with a condition to an integral value of the filter function and the SNR distribution, and wherein said filter intensity determining unit is configured to determine the filter function to proportionate a ratio between a minimum value and a maximum value of an SNR distribution on filtering objective data which is an object of the corresponding filtering having the mutually different intensity to a ratio between an integral value of a filter function for a minimum SNR which is applied to a part showing a minimum SNR on the filtering objective data and an integral value of a filter function for a maximum SNR which is applied to a part showing a maximum SNR on the filtering objective data with regarding the SNR distribution on the filtering objective data as an inverse number of an SD of a noise on a part having no signal of real space data after the sensitivity correction.

3. A data correction apparatus comprising:
a sensitivity correction unit configured to correct original data, the original data being obtained with a sensor of an image diagnostic apparatus, the sensor having a spatially non-uniform sensitivity distribution, to generate spatially uniform sensitivity data by applying an inverse distribution of the sensitivity distribution of the sensor to the original data;
a weighting function generating unit configured to generate a first weighting function corresponding to the non-uniform sensitivity distribution, and to generate a second weighting function which has an inverse distribution of the first weighting function;
a filtering unit configured to filter the spatially uniform sensitivity data using a filter;
a weighting unit configured to weight the spatially uniform sensitivity data before said filtering with the first weighting function to generate high SNR emphasized data in which data in a high SNR region is emphasized, and to weight the spatially uniform sensitivity data after said filtering with the second weighting function to generate low SNR emphasized data in which data in a low SNR region is emphasized; and
a combining unit configured to add the high SNR emphasized data and the low SNR emphasized data to generate corrected uniform sensitivity data in which uniformity of spatial noise distribution is enhanced.

4. The data correction apparatus according to claim 3, wherein the filter is a spatially invariant filter of which a parameter does not vary spatially.

5. The data correction apparatus according to claim 3, wherein the non-uniform sensitivity distribution is normalized so that the first weighting function has a maximum value of 1.

6. The data correction apparatus according to claim 3, wherein the non-uniform sensitivity distribution is normalized so that the first weighting function has a maximum value of 1 and a minimum value of 0.

7. A data correction apparatus comprising:
a sensitivity correction unit configured to correct original data, the original data being obtained with a sensor of an image diagnostic apparatus, the sensor having a spatially non-uniform sensitivity distribution, to generate spatially uniform sensitivity data by applying an inverse distribution of the sensitivity distribution of the sensor to the original data;
a weighting function generating unit configured to generate a first weighting function corresponding to the non-uniform sensitivity distribution, and to generate a second weighting function which has an inverse distribution of the first weighting function;
a weighting unit configured to weight the spatially uniform sensitivity data before filtering with the first weighting function to generate high SNR emphasized data in which data in a high SNR region is emphasized, and to weight the spatially uniform sensitivity data after filtering with the second weighting function to generate low SNR emphasized data in which data in a low SNR region is emphasized;
a filtering unit configured to filter the low SNR emphasized data using a filter; and
a combining unit configured to add the high SNR emphasized data and the filtered low SNR emphasized data to generate corrected uniform sensitivity data in which uniformity of spatial noise distribution is enhanced.

8. The data correction apparatus according to claim 7, wherein the filter is a spatially invariant filter of which a parameter does not vary spatially.

9. The data correction apparatus according to claim 7, wherein the non-uniform sensitivity distribution is normalized so that the first weighting function has a maximum value of 1.

10. The data correction apparatus according to claim 7, wherein the non-uniform sensitivity distribution is normalized so that the first weighting function has a maximum value of 1 and a minimum value of 0.

11. A data correction apparatus for correcting original data, the original data being obtained with a sensor of an image diagnostic apparatus, the sensor having a spatially non-uniform sensitivity distribution, the data correction apparatus comprising:
a weighting function generating unit configured to generate a first weighting function corresponding to the non-uniform sensitivity distribution, and to generate a second weighting function which has an inverse distribution of the first weighting function;
a filtering unit configured to filter the original data using a filter;
a weighting unit configured to weight the original data before filtering with the first weighting function to generate high SNR emphasized data in which data in a high SNR region is emphasized, and to weight the original data after filtering with the second weighting function to generate low SNR emphasized data in which data in a low SNR region is emphasized;
a combining unit configured to add the high SNR emphasized data and the low SNR emphasized data to generate a combined data; and
a sensitivity correction unit configured to correct the combined data, by applying an inverse distribution of the sensitivity distribution of the sensor to the combined data, to generate uniform sensitivity data in which uniformity of spatial noise distribution is enhanced.

12. The data correction apparatus according to claim 11, wherein the filter is a spatially invariant filter of which a parameter does not vary spatially.

13. The data correction apparatus according to claim 11, wherein the filter is a Wiener filter of which noise power as a parameter has spatial uniform distribution.

14. The data correction apparatus according to claim 11, wherein the non-uniform sensitivity distribution is normalized so that the first weighting function has a maximum value of 1.

15. The data correction apparatus according to claim 11, wherein the non-uniform sensitivity distribution is normalized so that the first weighting function has a maximum value of and a minimum value of 0.

16. A data correction apparatus for correcting original data, the original data being obtained with a sensor of an image diagnostic apparatus, the sensor having a spatially non-uniform sensitivity distribution, the data correction apparatus comprising:
   a weighting function generating unit configured to generate a first weighting function corresponding to the non-uniform sensitivity distribution, and to generate a second weighting function which has an inverse distribution of the first weighting function;
   a weighting unit configured to weight the original data with the first weighting function to generate high SNR emphasized data in which data in a high SNR region is emphasized, and to weight the original data with the second weighting function to generate low SNR emphasized data in which data in a low SNR region is emphasized;
   a filtering unit configured to filter the low SNR emphasized data using a filter;
   a combining unit configured to add the high SNR emphasized data and the filtered low SNR emphasized data to generate a combined data; and
   a sensitivity correction unit configured to correct the combined data, by applying an inverse distribution of the sensitivity distribution of the sensor to the combined data, to generate uniform sensitivity data in which uniformity of spatial noise distribution is enhanced.

17. The data correction apparatus according to claim 16, wherein the filter is a spatially invariant filter of which a parameter does not vary spatially.

18. The data correction apparatus according to claim 16, wherein the non-uniform sensitivity distribution is normalized so that the first weighting function has a maximum value of 1.

19. The data correction apparatus according to claim 16, wherein the non-uniform sensitivity distribution is normalized so that the first weighting function has a maximum value of 1 and a minimum value of 0.

20. A data correction method comprising:
   using at least one programmed computer to:
   correct original data, the original data being obtained with a sensor of an image diagnostic apparatus, the sensor having spatially non-uniform sensitivity distribution, to generate spatially uniform sensitivity data by applying an inverse distribution of the sensitivity distribution of the sensor to the original data;
   generate a first weighting function corresponding to the non-uniform sensitivity distribution and generate a second weighting function which has an inverse distribution of the first weighting function;
   filter the spatially uniform sensitivity data using a filter;
   weight the spatially uniform sensitivity data before filtering with the first weighting function to generate high SNR emphasized data in which data in a high SNR region is emphasized;
   weight the spatially uniform sensitivity data after filtering with the second weighting function to generate low SNR emphasized data in which data in a low SNR region is emphasized; and
   add the high SNR emphasized data and the low SNR emphasized data to generate corrected uniform sensitivity data in which uniformity of spatial noise distribution is enhanced.

21. A data correction method comprising:
   using at least one programmed computer to:
   correct an original data, the original data being obtained with a sensor of an image diagnostic apparatus, the sensor having spatially non-uniform sensitivity distribution, to generate spatially uniform sensitivity data by applying an inverse distribution of the sensitivity distribution of the sensor to the original data;
   generate a first weighting function corresponding to the non-uniform sensitivity distribution, and generate a second weighting function which has an inverse distribution of the first weighting function;
   weight the spatially uniform sensitivity data before filtering with the first weighting function to generate high SNR emphasized data in which data in a high SNR region is emphasized;
   weight the spatially uniform sensitivity data after filtering with the second weighting function to generate low SNR emphasized data in which data in a low SNR region is emphasized;
   filter the low SNR emphasized data using a filter; and
   add the high SNR emphasized data and the filtered low SNR emphasized data to generate corrected uniform sensitivity data in which uniformity of spatial noise distribution is enhanced.

22. A data correction method for correcting an original data, the original data being obtained with a sensor of an image diagnostic apparatus, the sensor having spatially non-uniform sensitivity distribution, the method comprising:
   use of at least one programmed computer to:
   generate a first weighting function corresponding to the non-uniform sensitivity distribution;
   generate a second weighting function which has an inverse distribution of the first weighting function;
   filter the original data using a filter;
   weight the original data before filtering with the first weighting function to generate high SNR emphasized data in which data in a high SNR region is emphasized;
   weight the original data after filtering with the second weighting function to generate low SNR emphasized data in which data in a low SNR region is emphasized;
   add the high SNR emphasized data and the low SNR emphasized data to generate a combined data; and
   correct the combined data, by applying an inverse distribution of the sensitivity distribution of the sensor to the combined data, to generate uniform sensitivity data in which uniformity of spatial noise distribution is enhanced.

23. A data correction method for correcting an original data, the original data being obtained with a sensor of an image diagnostic apparatus, the sensor having spatially non-uniform sensitivity distribution the method comprising:

use of at least one programmed computer to:
generate a first weighting function corresponding to the non-uniform sensitivity distribution;
generate a second weighting function which has an inverse distribution of the first weighting function;
weight the original data with the first weighting function to generate high SNR emphasized data in which data in a high SNR region is emphasized;
weight the original data with the second weighting function to generate low SNR emphasized data in which data in a low SNR region is emphasized;
fitter the low SNR emphasized data using a filter;
add the high SNR emphasized data and the filtered low SNR emphasized data to generate a combined data; and
correct the combined data, by applying an inverse distribution of the sensitivity distribution of the sensor to the combined data, to generate uniform sensitivity data in which uniformity of spatial noise distribution is enhanced.

* * * * *